(12) United States Patent
Morgan et al.

(10) Patent No.: US 8,486,070 B2
(45) Date of Patent: Jul. 16, 2013

(54) TELEMETRIC ORTHOPAEDIC IMPLANT

(75) Inventors: Robert L. Morgan, Nether Poppleton (GB); Mark David Wickham, Rampton (GB); Peter A. Brady, Shrewsbury (GB); Sied W. Janna, Memphis, TN (US); Gene Edward Austin, Bartlett, TN (US); Darren James Wilson, York (GB)

(73) Assignee: Smith & Nephew, Inc., Memphis, TN (US)

( * ) Notice: Subject to any disclaimer, the term of this patent is extended or adjusted under 35 U.S.C. 154(b) by 1153 days.

(21) Appl. No.: 12/064,546

(22) PCT Filed: Aug. 23, 2006

(86) PCT No.: PCT/US2006/033326
§ 371 (c)(1),
(2), (4) Date: Jul. 28, 2008

(87) PCT Pub. No.: WO2007/025191
PCT Pub. Date: Mar. 1, 2007

(65) Prior Publication Data
US 2008/0300597 A1    Dec. 4, 2008

Related U.S. Application Data

(60) Provisional application No. 60/710,550, filed on Aug. 23, 2005, provisional application No. 60/728,374, filed on Oct. 19, 2005, provisional application No. 60/816,675, filed on Jun. 27, 2006.

(51) Int. Cl.
*A61B 17/56* (2006.01)
(52) U.S. Cl.
USPC .......................................................... 606/62

(58) Field of Classification Search
USPC ......... 606/60, 62–64, 67, 68, 102; 623/16.11, 623/20.32, 20.35, 24; 607/60
See application file for complete search history.

(56) References Cited

U.S. PATENT DOCUMENTS

| 3,713,148 A | 1/1973 | Cardullo et al. |
| 3,727,209 A | 4/1973 | White et al. |

(Continued)

FOREIGN PATENT DOCUMENTS

| CN | 1127446 A | 7/1996 |
| CN | 101022760 A | 8/2007 |

(Continued)

OTHER PUBLICATIONS

Chinese Decision on Rejection for Chinese Patent Application 200680038574.1 issued Oct. 26, 2011 (English translation), 12 pages.

(Continued)

*Primary Examiner* — Eduardo C Robert
*Assistant Examiner* — David Comstock
(74) *Attorney, Agent, or Firm* — Fish & Richardson P.C.

(57) ABSTRACT

An instrumented orthopaedic implant, such as an intramedullary (IM) nail, is disclosed. The implant has the capacity to provide an accurate measurement of the applied mechanical load across the implant. The implant includes sensors and associated electronic components located in recesses on the outer surface of the implant. The implant houses the sensing apparatus, the interface circuitry, the data transmitter, and the power receiver. The hermetically sealed housing is adapted for implantation in the body of a patient. The implant is used with a controller which communicates with it by telemetry, and there is an acting unit connected to the electronic components which is adapted to carry out a function based upon a condition detected by the sensors.

20 Claims, 13 Drawing Sheets

U.S. PATENT DOCUMENTS

| | | |
|---|---|---|
| 3,976,060 A | 8/1976 | Hildebrandt et al. |
| 4,096,477 A | 6/1978 | Epstein et al. |
| 4,242,663 A | 12/1980 | Slobodin |
| 4,281,664 A | 8/1981 | Duggan |
| 4,361,153 A | 11/1982 | Slocum et al. |
| 4,441,498 A | 4/1984 | Nordling |
| 4,473,825 A | 9/1984 | Walton |
| 4,481,428 A | 11/1984 | Charlot |
| 4,494,545 A | 1/1985 | Slocum et al. |
| 4,510,495 A | 4/1985 | Sigrimis et al. |
| 4,513,743 A | 4/1985 | van Arragon et al. |
| 4,525,713 A | 6/1985 | Barletta et al. |
| 4,546,241 A | 10/1985 | Walton |
| 4,571,589 A | 2/1986 | Slocum et al. |
| 4,576,158 A | 3/1986 | Boland |
| 4,944,299 A | 7/1990 | Silvian |
| 4,952,928 A | 8/1990 | Carroll et al. |
| 4,991,682 A | 2/1991 | Kuntz et al. |
| 5,024,239 A | 6/1991 | Rosenstein |
| 5,030,236 A | 7/1991 | Dean |
| 5,042,504 A | 8/1991 | Huberti |
| 5,117,825 A | 6/1992 | Grevious |
| 5,197,488 A | 3/1993 | Kovacevic |
| 5,252,962 A | 10/1993 | Urbas et al. |
| 5,309,919 A | 5/1994 | Snell et al. |
| 5,326,363 A | 7/1994 | Aikins |
| 5,330,477 A | 7/1994 | Crook |
| 5,334,202 A | 8/1994 | Carter |
| 5,337,747 A | 8/1994 | Neftel |
| 5,360,016 A | 11/1994 | Kovacevic |
| 5,383,935 A | 1/1995 | Shirkhanzadeh |
| 5,416,695 A | 5/1995 | Stutman et al. |
| 5,423,334 A | 6/1995 | Jordan |
| 5,425,775 A | 6/1995 | Kovacevic |
| 5,456,724 A | 10/1995 | Yen et al. |
| 5,470,354 A | 11/1995 | Hershberger et al. |
| 5,481,262 A | 1/1996 | Urbas et al. |
| 5,518,008 A | 5/1996 | Cucchiaro et al. |
| 5,524,637 A | 6/1996 | Erickson |
| 5,533,519 A | 7/1996 | Radke et al. |
| 5,626,630 A | 5/1997 | Markowitz et al. |
| 5,630,835 A | 5/1997 | Brownlee |
| 5,681,313 A | 10/1997 | Diez |
| 5,695,496 A | 12/1997 | Orsak et al. |
| 5,720,746 A | 2/1998 | Soubeiran |
| 5,733,292 A | 3/1998 | Gustilo et al. |
| 5,735,887 A | 4/1998 | Barreras et al. |
| 5,741,315 A | 4/1998 | Lee et al. |
| 5,792,076 A | 8/1998 | Orsak et al. |
| 5,807,701 A | 9/1998 | Payne et al. |
| 5,833,603 A | 11/1998 | Kovacs et al. |
| 5,836,989 A | 11/1998 | Shelton |
| 5,873,843 A | 2/1999 | Draper |
| 5,904,708 A | 5/1999 | Goedeke |
| 5,935,171 A | 8/1999 | Schneider et al. |
| 5,944,745 A | 8/1999 | Rueter |
| 6,009,878 A | 1/2000 | Weijand et al. |
| 6,025,725 A | 2/2000 | Gershenfeld et al. |
| 6,034,295 A | 3/2000 | Rehberg et al. |
| 6,034,296 A | 3/2000 | Elvin et al. |
| 6,059,576 A | 5/2000 | Brann |
| 6,061,597 A | 5/2000 | Rieman et al. |
| 6,102,874 A | 8/2000 | Stone et al. |
| 6,111,520 A | 8/2000 | Allen et al. |
| 6,120,502 A | 9/2000 | Michelson |
| 6,135,951 A | 10/2000 | Richardson et al. |
| 6,143,035 A | 11/2000 | McDowell |
| 6,168,569 B1 | 1/2001 | McEwen et al. |
| 6,183,425 B1 | 2/2001 | Whalen et al. |
| 6,200,265 B1 | 3/2001 | Walsh et al. |
| 6,201,980 B1 | 3/2001 | Darrow et al. |
| 6,210,301 B1 | 4/2001 | Abraham-Fuchs et al. |
| 6,245,109 B1 | 6/2001 | Mendes et al. |
| 6,312,612 B1 | 11/2001 | Sherman et al. |
| 6,325,756 B1 | 12/2001 | Webb et al. |
| 6,327,501 B1 | 12/2001 | Levine et al. |
| 6,356,789 B1 | 3/2002 | Hinssen et al. |
| 6,369,694 B1 | 4/2002 | Mejia |
| 6,385,593 B2 | 5/2002 | Linberg |
| 6,402,689 B1 | 6/2002 | Scarantino et al. |
| 6,433,629 B2 | 8/2002 | Hamel et al. |
| 6,434,429 B1 | 8/2002 | Kraus et al. |
| 6,442,432 B2 | 8/2002 | Lee |
| 6,447,448 B1 | 9/2002 | Ishikawa et al. |
| 6,447,449 B1 | 9/2002 | Fleischman et al. |
| 6,449,508 B1 | 9/2002 | Sheldon et al. |
| 6,466,810 B1 | 10/2002 | Ward et al. |
| 6,477,424 B1 | 11/2002 | Thompson et al. |
| 6,482,154 B1 | 11/2002 | Haubrich et al. |
| 6,497,655 B1 | 12/2002 | Linberg et al. |
| 6,499,488 B1 | 12/2002 | Hunter et al. |
| 6,527,711 B1 | 3/2003 | Stivoric et al. |
| 6,529,127 B2 | 3/2003 | Townsend et al. |
| 6,535,766 B1 | 3/2003 | Thompson et al. |
| 6,539,253 B2 | 3/2003 | Thompson et al. |
| 6,553,262 B1 | 4/2003 | Lang et al. |
| 6,567,703 B1 | 5/2003 | Thompson et al. |
| 6,573,706 B2 | 6/2003 | Mendes et al. |
| 6,583,630 B2 | 6/2003 | Mendes et al. |
| 6,602,191 B2 | 8/2003 | Quy |
| 6,610,096 B2 | 8/2003 | MacDonald |
| 6,636,769 B2 | 10/2003 | Govari et al. |
| 6,638,231 B2 | 10/2003 | Govari et al. |
| 6,641,540 B2 | 11/2003 | Fleischman et al. |
| 6,652,464 B2 | 11/2003 | Schwartz et al. |
| 6,658,300 B2 | 12/2003 | Govari et al. |
| 6,667,725 B1 | 12/2003 | Simons et al. |
| 6,675,044 B2 | 1/2004 | Chen |
| 6,682,490 B2 | 1/2004 | Roy et al. |
| 6,694,180 B1 | 2/2004 | Boesen |
| 6,706,005 B2 | 3/2004 | Roy et al. |
| 6,712,778 B1 | 3/2004 | Jeffcoat et al. |
| 6,738,671 B2 | 5/2004 | Christophersom et al. |
| 6,749,568 B2 | 6/2004 | Fleischman et al. |
| 6,764,446 B2 | 7/2004 | Wolinsky et al. |
| 6,766,200 B2 | 7/2004 | Cox |
| 6,783,499 B2 | 8/2004 | Schwartz |
| 6,790,372 B2 | 9/2004 | Roy et al. |
| 6,793,659 B2 | 9/2004 | Putnam |
| 6,804,552 B2 | 10/2004 | Thompson et al. |
| 6,807,439 B2 | 10/2004 | Edwards et al. |
| 6,810,753 B2 | 11/2004 | Valdevit et al. |
| 6,819,247 B2 | 11/2004 | Birnbach et al. |
| 6,821,299 B2 | 11/2004 | Kirking et al. |
| 6,834,436 B2 | 12/2004 | Townsend et al. |
| 6,855,115 B2 | 2/2005 | Fonseca et al. |
| 6,864,802 B2 | 3/2005 | Smith et al. |
| 6,895,281 B1 | 5/2005 | Amundson et al. |
| 6,926,670 B2 | 8/2005 | Rich et al. |
| 6,939,299 B1 | 9/2005 | Petersen et al. |
| 6,968,743 B2 | 11/2005 | Rich et al. |
| 6,994,672 B2 | 2/2006 | Fleischman et al. |
| 7,001,346 B2 | 2/2006 | White |
| 7,027,871 B2 | 4/2006 | Burnes et al. |
| 7,034,694 B2 | 4/2006 | Yamaguchi et al. |
| 7,097,662 B2 | 8/2006 | Evans |
| 7,147,604 B1 | 12/2006 | Allen et al. |
| 7,151,914 B2 | 12/2006 | Brewer |
| 7,182,736 B2 | 2/2007 | Roy |
| 7,190,273 B2 | 3/2007 | Liao et al. |
| 7,195,645 B2 | 3/2007 | DiSilvestro et al. |
| 7,209,790 B2 | 4/2007 | Thompson et al. |
| 7,212,133 B2 | 5/2007 | Goetz et al. |
| 7,218,232 B2 | 5/2007 | DiSilvestro |
| 7,229,415 B2 | 6/2007 | Schwartz |
| 7,256,695 B2 | 8/2007 | Hamel |
| 7,333,013 B2 | 2/2008 | Berger |
| 7,357,037 B2 | 4/2008 | Hnat et al. |
| 7,474,223 B2 | 1/2009 | Nycz et al. |
| 7,559,951 B2 | 7/2009 | DiSilvestro et al. |
| 7,729,758 B2 | 6/2010 | Haller et al. |
| 7,756,579 B2 | 7/2010 | Nitzan et al. |
| 7,780,613 B2 | 8/2010 | Sherman |
| 8,007,450 B2 | 8/2011 | Williams |
| 2001/0047125 A1 | 11/2001 | Quy |
| 2002/0099359 A1 | 7/2002 | Santini, Jr. et al. |
| 2002/0116080 A1 | 8/2002 | Birnbach et al. |

| | | |
|---|---|---|
| 2002/0138153 A1 | 9/2002 | Koniuk |
| 2002/0151978 A1 | 10/2002 | Zacouto et al. |
| 2002/0170193 A1 | 11/2002 | Townsend et al. |
| 2003/0040806 A1 | 2/2003 | MacDonald |
| 2003/0069644 A1 | 4/2003 | Kovacevic et al. |
| 2003/0105470 A1 | 6/2003 | White |
| 2003/0120150 A1 | 6/2003 | Govari |
| 2003/0136417 A1 | 7/2003 | Fonseca et al. |
| 2003/0143775 A1 | 7/2003 | Brady |
| 2003/0178488 A1 | 9/2003 | Southard |
| 2003/0229381 A1 | 12/2003 | Hochmair et al. |
| 2004/0008123 A1 | 1/2004 | Carrender et al. |
| 2004/0011137 A1 | 1/2004 | Hnat et al. |
| 2004/0014456 A1 | 1/2004 | Vaananen |
| 2004/0019382 A1 | 1/2004 | Amirouche |
| 2004/0073137 A1 | 4/2004 | Lloyd et al. |
| 2004/0073221 A1 | 4/2004 | Biscup |
| 2004/0094613 A1 | 5/2004 | Shiratori et al. |
| 2004/0113790 A1 | 6/2004 | Hamel et al. |
| 2004/0116837 A1 | 6/2004 | Yamaguchi et al. |
| 2004/0152972 A1 | 8/2004 | Hunter |
| 2004/0176815 A1 | 9/2004 | Janzig et al. |
| 2004/0186396 A1 | 9/2004 | Roy et al. |
| 2004/0204647 A1 | 10/2004 | Grupp et al. |
| 2004/0231420 A1 | 11/2004 | Xie et al. |
| 2004/0243148 A1 | 12/2004 | Wasielewski |
| 2004/0249315 A1 | 12/2004 | Damen |
| 2005/0010139 A1 | 1/2005 | Aminian et al. |
| 2005/0010299 A1 | 1/2005 | Disilvestro |
| 2005/0010300 A1 | 1/2005 | Disilvestro et al. |
| 2005/0010301 A1 | 1/2005 | Sisilvestro et al. |
| 2005/0010302 A1 | 1/2005 | Dietz |
| 2005/0012610 A1 | 1/2005 | Liao et al. |
| 2005/0012617 A1 | 1/2005 | DiSilvestro et al. |
| 2005/0015014 A1 | 1/2005 | Fonseca et al. |
| 2005/0061079 A1 | 3/2005 | Schulman |
| 2005/0080335 A1 | 4/2005 | Simon et al. |
| 2005/0099290 A1 | 5/2005 | Govari |
| 2005/0101833 A1 | 5/2005 | Hsu et al. |
| 2005/0113932 A1 | 5/2005 | Kovacevic |
| 2005/0131397 A1 | 6/2005 | Levin |
| 2005/0187482 A1 | 8/2005 | O'Brien et al. |
| 2005/0194174 A1 | 9/2005 | Hipwell, Jr. et al. |
| 2005/0234555 A1 | 10/2005 | Sutton et al. |
| 2005/0247319 A1 | 11/2005 | Berger |
| 2005/0273170 A1 | 12/2005 | Navarro et al. |
| 2005/0288727 A1 | 12/2005 | Penner |
| 2006/0009656 A1 | 1/2006 | Zhang |
| 2006/0009856 A1 | 1/2006 | Sherman et al. |
| 2006/0030771 A1 | 2/2006 | Levine |
| 2006/0032314 A1 | 2/2006 | Hnat et al. |
| 2006/0043178 A1 | 3/2006 | Tethrake et al. |
| 2006/0043179 A1 | 3/2006 | Nycz et al. |
| 2006/0047283 A1 | 3/2006 | Evans, III et al. |
| 2006/0052782 A1 | 3/2006 | Morgan et al. |
| 2006/0058627 A1 | 3/2006 | Flaherty |
| 2006/0065739 A1 | 3/2006 | Falls et al. |
| 2006/0069436 A1 | 3/2006 | Sutton et al. |
| 2006/0069447 A1 | 3/2006 | Disilvestro et al. |
| 2006/0109105 A1 | 5/2006 | Varner et al. |
| 2006/0111291 A1 | 5/2006 | DiMauro et al. |
| 2006/0119481 A1 | 6/2006 | Tethrake et al. |
| 2006/0129050 A1 | 6/2006 | Martinson et al. |
| 2006/0142656 A1 | 6/2006 | Malackowski et al. |
| 2006/0145871 A1 | 7/2006 | Donati et al. |
| 2006/0174712 A1 | 8/2006 | O'Brien et al. |
| 2006/0177956 A1 | 8/2006 | O'Brien et al. |
| 2006/0190080 A1 | 8/2006 | Danoff et al. |
| 2006/0196277 A1 | 9/2006 | Allen et al. |
| 2006/0200030 A1 | 9/2006 | White et al. |
| 2006/0200031 A1 | 9/2006 | White et al. |
| 2006/0232408 A1 | 10/2006 | Nycz et al. |
| 2006/0235310 A1 | 10/2006 | O'Brien et al. |
| 2006/0241354 A1 | 10/2006 | Allen |
| 2006/0244465 A1 | 11/2006 | Krob et al. |
| 2006/0260401 A1 | 11/2006 | Xie et al. |
| 2006/0271199 A1 | 11/2006 | Johnson |
| 2006/0283007 A1 | 12/2006 | Cros et al. |
| 2006/0287602 A1 | 12/2006 | O'Brien et al. |
| 2006/0287700 A1 | 12/2006 | White et al. |
| 2007/0038051 A1 | 2/2007 | Talman et al. |
| 2007/0078497 A1 | 4/2007 | Vandanacker |
| 2007/0089518 A1 | 4/2007 | Ericson et al. |
| 2007/0090543 A1 | 4/2007 | Condie et al. |
| 2007/0100215 A1 | 5/2007 | Powers et al. |
| 2007/0123938 A1 | 5/2007 | Haller et al. |
| 2007/0129769 A1 | 6/2007 | Bourget et al. |
| 2007/0180922 A1 | 8/2007 | Crottet et al. |
| 2007/0208544 A1 | 9/2007 | Kulach et al. |
| 2007/0219639 A1 | 9/2007 | Otto et al. |
| 2008/0086145 A1 | 4/2008 | Sherman et al. |
| 2008/0105874 A1 | 5/2008 | Wang et al. |
| 2008/0161729 A1 | 7/2008 | Bush |
| 2008/0208516 A1 | 8/2008 | James |
| 2009/0131838 A1 | 5/2009 | Fotiadis et al. |
| 2009/0222050 A1 | 9/2009 | Wolter et al. |
| 2010/0152621 A1 | 6/2010 | Janna et al. |

FOREIGN PATENT DOCUMENTS

| | | |
|---|---|---|
| DE | 19855254 | 6/2000 |
| EP | 0062459 B1 | 12/1986 |
| EP | 1023872 A2 | 8/2000 |
| EP | 1099415 A | 5/2001 |
| EP | 0959956 B1 | 12/2001 |
| EP | 1256316 | 11/2002 |
| EP | 1256316 A1 | 11/2002 |
| EP | 1309960 | 5/2003 |
| EP | 1331903 B1 | 8/2003 |
| EP | 1366712 A1 | 12/2003 |
| EP | 1495456 | 1/2005 |
| EP | 1502540 A1 | 2/2005 |
| EP | 0987047 B1 | 4/2005 |
| EP | 1535039 | 6/2005 |
| EP | 1541095 A2 | 6/2005 |
| EP | 1570781 | 9/2005 |
| EP | 1570781 A1 | 9/2005 |
| EP | 1570782 A2 | 9/2005 |
| EP | 1582183 A1 | 10/2005 |
| EP | 1586287 A2 | 10/2005 |
| EP | 1611835 A2 | 1/2006 |
| EP | 1642550 A2 | 4/2006 |
| EP | 1704893 A1 | 9/2006 |
| EP | 1738716 A2 | 1/2007 |
| EP | 1765204 | 3/2007 |
| EP | 1377340 | 5/2007 |
| EP | 1803394 A2 | 7/2007 |
| EP | 1830303 | 9/2007 |
| WO | 82/00378 | 2/1982 |
| WO | WO 90/06720 A1 | 6/1990 |
| WO | WO9621397 A1 | 7/1996 |
| WO | 96/29007 | 9/1996 |
| WO | WO 96/26678 | 9/1996 |
| WO | WO 96/29007 | 9/1996 |
| WO | WO 97/14367 | 4/1997 |
| WO | WO 97/20512 | 6/1997 |
| WO | WO9843701 A1 | 10/1998 |
| WO | WO 00/18317 A3 | 4/2000 |
| WO | WO 00/19888 | 4/2000 |
| WO | WO 00/30534 | 6/2000 |
| WO | WO 00/32124 | 6/2000 |
| WO | WO 01/19248 A1 | 3/2001 |
| WO | WO 01/37733 A2 | 5/2001 |
| WO | WO 02/03347 A1 | 1/2002 |
| WO | WO 02/28082 A1 | 5/2002 |
| WO | WO 02/056763 A3 | 7/2002 |
| WO | 02/058551 | 8/2002 |
| WO | WO 02/061705 A1 | 8/2002 |
| WO | 03/008570 | 1/2003 |
| WO | WO 03/003145 A2 | 1/2003 |
| WO | WO 03/044556 A2 | 5/2003 |
| WO | WO 03/085617 A1 | 10/2003 |
| WO | WO 2004/005872 A2 | 1/2004 |
| WO | 2004/014456 | 2/2004 |
| WO | 2004/014456 A2 | 2/2004 |
| WO | WO 2004/052453 A1 | 6/2004 |
| WO | WO 2004/052456 A1 | 6/2004 |
| WO | WO 2004/077073 A2 | 9/2004 |
| WO | WO 2005/007025 A | 1/2005 |

| | | |
|---|---|---|
| WO | WO 2005/013851 A2 | 2/2005 |
| WO | WO 2005/039440 A2 | 5/2005 |
| WO | 2005/074821 | 8/2005 |
| WO | WO 2005/074821 A2 | 8/2005 |
| WO | 2005/084544 | 9/2005 |
| WO | WO 2005/084544 A1 | 9/2005 |
| WO | WO 2005/104997 A2 | 11/2005 |
| WO | WO 2005/120203 A2 | 12/2005 |
| WO | 2006/010037 | 1/2006 |
| WO | WO 2006/010037 A2 | 1/2006 |
| WO | 2006/045080 | 4/2006 |
| WO | 2006/045607 | 5/2006 |
| WO | WO 2006/049796 A2 | 5/2006 |
| WO | WO 2006/052765 A2 | 5/2006 |
| WO | WO 2006/055547 A2 | 5/2006 |
| WO | 2006/063156 | 6/2006 |
| WO | 2006/089069 | 8/2006 |
| WO | WO 2006/086113 A2 | 8/2006 |
| WO | WO 2006/086114 A2 | 8/2006 |
| WO | WO 2006/094273 A2 | 9/2006 |
| WO | WO 2006/096582 A1 | 9/2006 |
| WO | WO 2006/110798 A2 | 10/2006 |
| WO | WO 2006/113660 A1 | 10/2006 |
| WO | WO2006131302 A1 | 12/2006 |
| WO | 2007/009088 | 1/2007 |
| WO | WO 2007/002185 A2 | 1/2007 |
| WO | WO 2007/002224 A2 | 1/2007 |
| WO | WO 2007/002225 A2 | 1/2007 |
| WO | WO 2007/008493 A1 | 1/2007 |
| WO | 2007/025191 | 3/2007 |
| WO | WO 2007/025191 A1 | 3/2007 |
| WO | WO 2007/030489 A1 | 3/2007 |
| WO | WO 2007/036318 A1 | 4/2007 |
| WO | WO2007041124 A1 | 4/2007 |
| WO | WO 2007/061890 A2 | 5/2007 |
| WO | 2007/090543 | 8/2007 |
| WO | 2008/105874 | 9/2008 |
| WO | 2009/098768 | 8/2009 |

OTHER PUBLICATIONS

Japanese Notice of Reasons for Rejection for Application No. 2008-528223 mailed Nov. 1, 2011 (Engligh translation), 3 pages.
Office Action for U.S. Appl. No. 12/528,243, mailed May 11, 2012.
Office Action for U.S. Appl. No. 11/718,588, mailed Jul. 16, 2012.
Decision of Rejection for Japanese Application 2008-528223, mailed Jul. 24, 2012.
International Search Report for International Application PCT/US2006/033326, dated Dec. 13, 2006, 5 pages.
International Preliminary Report on Patentability for International Application PCT/US2006/033326, dated Feb. 26, 2008, 9 pages.
Written Opinion of the International Searching Authority for International Application PCT/US2006/033326, mailed Feb. 23, 2008, 8 pages.
International Preliminary Report on Patentability for International Application No. PCT/US2009/032540, dated Aug. 3, 2010, 5 pages.
Written Opinion of the International Search Authority for International Application PCT/US2009/032540, dated Aug. 1, 2010, 4 pages.
Written Opinion of the International Search Authority for International Application PCT/US2008/075316, dated Mar. 6, 2010, 6 pages.
Office Action for U.S. Appl. No. 12/528,243, mailed Jun. 23, 2011, 10 pages.
Office Action for U.S. Appl. No. 11/718,588, mailed Dec. 8, 2010, 9 pages.
Final Office Action for U.S. Appl. No. 11/718,588, mailed May 5, 2011, 16 pages.
Office Action for U.S. Appl. No. 11/718,588, mailed Dec. 15, 2011, 17 pages.
International Search Report for International Application PCT/US2009/032540 dated Apr. 29, 2009, 3 pages.
Global market for RFID in healthcare 2006-2016 by value: Source: IDTechEx, RFID in Healthcare 2006-2016, May 1, 2006.
Fruin, et al, "Validity of a Multi-Sensor Armband in Estimating Rest and Exercise Energy Expenditure", Am Coll Sports Med, vol. 36, 6, pp. 1063-1069, 2004.
Jakicic, et al, "Evaluation of the SenseWear Pro Armband™ to Assess Energy Expenditure during Exercise", Med. Sci. Sports Exerc.; vol. 36,5, pp. 897-904, 2004.
Nachemson et al., "Intravital wireless telemetry of axial forces in Harrington distraction rods in patients with idiopathic scoliosis", J.Bone Jt Surg. 53A, 445-464 (Apr. 1971).
Burny, et al., "Smart orthopedic implants", Orthopedics, Dec. 2005; 28 (12):1401.
Rydell, "Forces Acting on the Femoral Head Prosthesis", Acta Orthop Scand, Suppl. 88, 1966.
Lanyon, et al., "In Vivo Strain Measurements from Bone and Prosthesis following Total Hip Replacement", The Journal of Bone and Joint Surgery, vol. 63-A, No. 6, pp. 989-1000, 1981.
Carlson, et al., "A Radio Telemetry Device for Monitoring Cartilage Surface Pressures in the Human Hip", IEEE Trans. on Biomed. Engrg.,vol. BME-21, No. 4, pp. 257-264, Jul. 1974.
Carlson, et al, "A look at the prosthesis-cartilage interface: design of a hip prosthesis containing pressure transducers", J Biomed Mater Res. 1974; 8(4 pt 2): 261-269.
English, et al., "In vivo records of hip loads using a femoral implant with telemetric output (a preliminary report)," J Biomed Eng. 1979; 1(2):111-115,.
Rushfeldt, et al., Improvd Techniques for Measuring in Vitro Geometry and Pressure Distribution in Human Acetabulum-II. Instrumented . . . J Biomechanics No. 14, pp. 315-323, 1981.
Hodge, et al., "Preliminary In Vivo Pressure Measurements in a Human Acetabulum", Proceedings of 31 st Annual Meeting, Orthopaedic Research Society, 1985.
Hodge, et al., "Contact Pressures in the Human Hip Joint Measured In Vivo", Proc. of National Academy of Science, U.S.A., No. 83, pp. 2879-2883, 1986.
Brown, et al., "In Vivo Load Measurements on a Total Hip Prosthesis", Proceedings of the 31 st Meeting, Orthopaedic Research Society, 1985.
Davy, et al., "Telemetric Force Measurements across the Hip after Total Arthroplasty", Journal of Bone and Joint Surgery, vol. 70-A, No. 1, Jan. 1988: 45-50.
Taylor, et al., "Telemetry of forces from proximal femoral replacements and relevance to fixation", J Biomech. 1997; 30:225-234.
Bergmann, et al., "Multichannel Strain Gauge Telemetry for Orthopaedic Implants", Technical Note, J. Biomechanics, vol. 21, No. 2, pp. 169-176, 1988.
Rohlmann, et al., "Telemeterized Load Measurement Using Instrumented Spinal Internal Fixators in a Patient with Degenerative Instability", Spine, vol. 20, No. 24, 1995.
Berkman, et al., "Biomedical Micropressor with Analog I/O", Inter. Solid-State Circuits Conf. Digest of Technical Papers, pp. 168-169, 1981.
Dorman, et al., "A Monolithic Signal Processor for a Neurophysiological Telemetry System", IEEE Journal of Solid-State Circuits, vol. 20, pp. 1185-1193, 1985.
Gschwend, et al., "A General Purpose Implantable Multichannel Telemetry System for Physiological Research", Biotelemetry Patient Monitoring, vol. 6, pp. 107-117, 1979.
Cook, et al., "A Custom Microprocessor for Implantable Telemetry Systems", Proc of the IEEE Symp. On Computer-Based Medical Systems, pp. 412-417, Jun. 1990.
Brown, et al., "Telemetering In Vivo Loads from Nail Plate Implants", J. Biomechanics, vol. 15, No. 11, pp. 815-823, 1982.
Fernald, et al., "A System Architecture for Intelligent Implantable Biotelemetry Instruments", Proc. IEEE Eng in Medicine and Biology Soc. Annual Conf., pp. 1411-1412, 1989.
Rohlmann, et al., "Influence of load carrying on loads in internal spinal fixators", J Biomech. 2000; 33:1099-1104.
Rohlmann, et al., "Loads on an internal spinal fixation device during walking", J Biomech, 1997; 30:41-47.
Schneider, et al, "Loads acting in an intramedullary nail during fracture healing in the human femur", Journal of Biomechanics 34, 2001, pp. 849-857.
Heinlein, et al., "An instrumented knee endoprosthesis for measuring loads in vivo", EORS 2004, 51st Annual Meeting of the Orthopaedic research Society, Aug. 2007, 1 page.

Townsend, et al., Multichannel, Programmable, Microprocessor Based Strain Gauge . . . , 18th Ann. Int Conf. IEEE Eng. in Med & Biology Soc. Oct. 31-Nov. 3,.1996, Amsterdam.

Mendes, et al., "IntelliJoint System for monitoring displacement in biologic system", Biomed Bytes 2002 (4), pp. 69-70.

Cristofolini, et al., "A novel transducer for the measurement of cement-prosthesis interface forces in cemented . . . ", Medicial Eng & Physics vol. 22, Sept 7, 2000, pp. 493-501.

Müller, Otto, et al., "Three-dimensional measurements of the pressure distribution in artificial joints with a capacitive sensor array", J Biomech, vol. 37, Oct. 2004, pp. 1623-1625.

Bergmann, et al., "Frictional Heating of Total Hip Implants. Part 1: Measurements in Patients," Journal of Biomechanics, vol. 34, Issue 4, Apr. 2001, pp. 421-428.

Rohlmann, et al., "In vitro load measurement using an instrumented spinal fixation device", Medical Engineering & Physics, vol. 18, Issue 6, Sep. 1996, pp. 485-488.

Burny, et al., "Concept, design and fabrication of smart orthopaedic implants", Medical Engineering & Physics, 22 (2000), pp. 469-479.

Townsend, et al., "Remotely powered multichannel microprocessor based telemetry systems for smart implantable devices and smart structures," Proc. SPIE vol. 3673, pp. 150-156 (Mar. 1999).

D'Lima, et al., "An implantable telemetry device to measure intra-articular tibial forces", J Biomech. Feb. 2005; 38(2): pp. 299-304.

Bergmann, et al., "Hip Joint Contact Forces during Stumbling", Langenbecks Arch Surg. Feb. 2004; 389(1): 53-9. Epub Nov. 19, 2003.

Stansfield, et al., "Direct comparison of calculated hip joint contact forces with those measured using instrumented implants . . . " J Biomech. Jul. 2003; 36(7):929-36.

Heller, et al., "Musculo-skeletalloading conditions at the hip during walking and stair climbing", J Biomech. Jul. 2001; 34(7):883-93.

Bergmann, et al., "Hip Contact Forces and Gait Patterns from Routing Activities", J. Biomech. Jul. 2001; 34(7):859-71.

Bergmann, et al., "Frictional Heating of Total Hip Implants. Part 2: Finite Element Study," J Biomech. Apr. 2001; 34(4):429-35.

Park, et al, "Hip muscle co-contraction: evidence from concurrent in vivo pressure measurement and force estimation", Gait Posture. Dec. 1999; 10(3):211-22.

Graichen, et al., "Hip endoprosthesis for in vivo measurement of joint force and temperature", J Biomech Oct. 1999; 32(10):1113-7.

Krebs, et al., "Hip Biomechanics during Gait", J Orthop & Sports Phys Ther. Jul. 1998; 28(1):51-9.

Tackson, et al., "Acetabular pressures during hip arthritis exercises", Arthritis Care & Res. Oct. 1997; 10(5):308-19.

Kotzar, et al, "Torsional loads in the early postoperative period following total hip replacement", J Orthop Res. Nov. 1995; 13(6):945-55.

Bergmann, et al, "Is staircase walking a risk for the fixation of hip implants?," J Biomech, May 1995; 28(5):535-53.

Brand, et al, "Comparison of hip force calculations and measurements in the same patient", J Arthroplasty, Feb. 1994; 9(1):45-51.

Bergmann, et al., "Hip joint loading during walking and running, measured in two patients", J Biomech, Aug. 1993; 26(8):969-90.

Graichen, et al., "Four-channel telemetry system for in vivo measurement of hip joint forces", J Sioment Eng, Sep. 1991; 13(5):370-4.

Kotzar, et al., "Telemeterized in vivo hip joint force data: a report on two patients after total hip surgery", J Orthop Res., Sep. 1991, 9(5):621-33.

Morrell, et al., "Corroboration of in vivo cartilage pressures with implacations for synovial joint tribology and . . . ", Proc Natl Acad Sci USA, Oct. 11, 2005; 102(41 ):14819-24.

McGibbon, et al., "Cartilage degeneration in relation to repetitive pressure: case study of a unilateral hip hemiarthroplasty patient". J Arthroplasty, Jan. 1999, 14(1):52-8.

Lu, et al., "Influence of muscle activity on the forces in the femur: An in vivo study", J Biomech, Nov.-Dec. 1997; 30(11-12):1101-6.

Taylor, et al., "Telemetry of forces from proximal femoral replacements and relevance to fixation", J Biomech, Mar. 1997; 30(3):225-34.

Puers, et al., "A telemetry system for the detection of hip prosthesis loosening by vibration analysis", Sensors and Actuators 85 (2000) 42-47.

Aminian K, et al., "Temporal Feature Estimation During Walking Using Miniature Accelerometers . . . " Med Biol Eng Comput, 1999, 37, 686-691.

Bussmann JBJ, et al., "Analysis and Decomposition of Signals Obtained by Thigh-Fixed Uni-Axial Accelerometry During Normal Walking," Med Biol Eng Comput, 2000, 38, 632-638.

Petrofsky JS, et al., "Joint Acceleration during Gait in Relation to Age," Eur J Appl Physiology. 2004, 92: 254-262.

Patent Application for U.S. Appl. No. 60/710,550, filed Aug. 23, 2005.

International Search Report for International Application PCT/US2005/040052 dated Jun. 22, 2006, 8 pages.

Written Opinion of the International Search Authority issued in PCT/US2005/040052 on May 20, 2006, 9 pages.

International Preliminary Report on Patentability issued in PCT/US2005/040052 on May 8, 2007, 10 pages.

International Search Report and Written Opinion for International Application PCT/US2007/062757 dated Nov. 19, 2007, 8 pages.

International Search Report for International Application PCT/US2008/075316 dated Dec. 3, 2008, 2 pages.

International Search Report for International Application PCT/US2008/032540 dated Apr. 29, 2009, 3 pages.

International Preliminary Report on Patentability for International Application No. PCT/US2007/062757, mailed Aug. 29, 2009, 6 pages.

International Preliminary Report on Patentability for International Application No. PCT/US2008/075316, mailed Mar. 9, 2010, 7 pages.

Bergmann, et al, "Design and Calibration of Load Sensing Orthopaedic Implants," Journal of Biomechanical Engineering, Apr. 2008, vol. 130, 9 pages.

Catrysse, M., et al., "An Inductive Powering System with Integrated Bidirectional Datatransmission," Sensors and Actuators A: Physical, vol. 115, Issues 2-3, Sep. 21, 2004, pp. 221-229, The 17th European Conference on Solid-State Transducers.

Claes, L.E., and Cunningham, J.L., "Monitoring the Mechanical Properties of Healing Bone," Clin Orthop Relat res (2009) 467:1964-1971.

Kao-Shang Shih, et al, "Influence of Muscular Contractions on the Stress Analysis of Distal Femoral Interlocking Nailing," Clinical Biomechanics, 23 (2008) 38-44.

Westerhoff, P., "An Instrumented Implant for in vivo Measurement of Contact Forcdes and Contact Moments in the Shoulder Joint," Medical Engineering & Physics, 31 (2009) 207-213.

Swedberg, Claire, "Surgeon Designs System to Monitor Orthopaedic Implants and Promote Healing," RFID Journal, reprinted from http://www.rfidjournal.com/article/articleprint/3978/-1/1 on Mar. 26, 2008, 2 pages.

Rapp, Susan M., "Smart Implants to Provide Feedback, Measure Joint Loads, Detect Infection," Orthopedics Today, 2008, reprinted from http://www.orthosupersite.com/view.asp?rID=28657 on Jun. 6, 2008, 3 pages.

Seide, K., et al., "An Intelligent Internal Fixator System for Long Bones," 52nd Annual Meeting of the Orthopaedic Research Society, Paper No. 1698.

Rorie, J.F., et al, "A Telemetric Instrumentation System for Orthopaedic Implants," Apr. 19, 1995, 15 pages.

Arms, S.W., et al., "Wireless Strain Measurement Systems—Applications and Solutions," presented at NSF-ESF Joint Conference on Structural Health Monitoring, Strasbourg, France, Oct. 3-5, 2003.

Yang, G.Y., et al, "Design of Microfabricated Strain Gauge Array to Monitor Bone Deformation In Vitro and In Vivo," Proceedings of the Fourth IEEE Symposium on Bioinformatics and Bioengineering, May 19-21, 2004, 8 pages.

Einhorn, T.A., "The Cell and Molecular Biology of Fracture Healing," Clin Orthop, 1998: Suppl: 355:7-21.

Elvin, N., et al., "A Self-Powered Mechanical Strain Energy Sensor," Smart Matter Struct 2001; 10:1-7.

Kummer, F. J., et al., "Development of a Telemeterized Should Prosthesis," Clin Orthop Relat Res., Sep. 1996 (330):31-4.

Morris BA, D'Iima, D.D , J., Kovacevic, N., Arms, S.W., Townsend, C.P., and Colwell, C.W. Jr., "e-Knee: Evolution of the Electronic Knee Prosthesis," J Bone Joint Surg., 83:62-66, 2000.

Kaufman, K., Irby, S.E., and Colwell, C.W., "Instrumented Implant for Measuring Tibiofemoral Forces," J. Biomechanics, 29:667-671, 1996.

Taylor, S.J.G., Walker, P.S., Perry, J.S., Cannon, S.R., and Woledge, R., "The Forces in the Distal Femur and the Knee During Walking and Other Activities Measured by Telemetry," the Journal of Arthroplasty, 13:428-437, 1998.

SRI Consulting, "RFID Technologies", 2004; and Silicon Chip Online, "RFID Tags—How They Work." reprinted from http://www.siliconchip.com.au/cms/A30750/article.html.

Global market for RFID in healthcare 2006-2016 by value: Source: IDTechEx, RFIDfid in Healthcare 2006-2016.

Healthcare RFID Medical Microchip, Yenra, Apr. 30, 2003, reprinted from http://www.yenra.com/healthcare-rfid-medical-microchip/.

Verichip System, Product of VeriChip Corp., reprinted from http://www.verichipcorp.com/content/solutions/verichip reprinted on Apr. 26, 2011.

Sub-dermal RFID, Yenra, Sep. 25, 2003, reprinted from http://www.yenra.com/subdermalrfid/.

Clyde Church, "Radio Frequency Identification (RFID) Tracking of Orthopaedic Inventories Fact or Fiction, Today and Tomorrow," BONE Zone, Spring 2004, pp. 35-40.

Luis Figarella, Kirk Kikirekov, Heinrich Oehlmann, Radio Frequency Identification (RFID) in Health Care, Benefits, Limitations, Recommendations, A Health Industry Business Communications Council HIBCC White Paper (2006).

Alex Macario; Dean Morris; Sharon Morris "Initial Clinical Evaluation of a Handheld Device for Detecting Retained Surgical Gauze Sponges Using Radiofrequency Identification Technology" Arch Surg., 2006; 141:659-662.

Patricia Kaeding "RFID medical devices—Opportunities and challenges," Published Oct. 19, 2005, Wisconsin Technology Network, http://wistechnology.com.

First Office Action for Chinese Application No. 200680038574.1, mailed Oct. 9, 2009, 16 pages.

Second Office Action for Chinese Application No. 200680038574.1, mailed Jul. 7, 2011, 8 pages.

First Office Action for Chinese Application No. 200880115437.2, mailed Nov. 22, 2012.

Office Action for Chinese Application No. 200980112399, mailed Dec. 25, 2012.

Patent Examination Report No. 1 for Australian Application No. 2009209045, mailed Nov. 29, 2012.

Office Action for U.S. Appl. No. 12/865,657, mailed Jan. 23, 2013.

Office Action for U.S. Appl. No. 12/528,243, mailed Dec. 19, 2012.

Official Inquiry for Japanese Application No. 2012-23327, mailed Apr. 9, 2013.

Notice of Reexamination for Chinese Application No. 200680038574.1, mailed Mar. 12, 2013.

TELEMETRIC ORTHOPAEDIC IMPLANT

CROSS-REFERENCE TO RELATED APPLICATIONS

This application is a National Phase of International Application No. PCT/US2006/033326, filed Aug. 23, 2006. This application claims the benefit of U.S. Provisional Application No. 60/710,550, filed on Aug. 23, 2005; U.S. Provisional Application No. 60/728,374, filed on Oct. 19, 2005; and U.S. Provisional Application No. 60/816,675, filed on Jun. 27, 2006. The disclosure of each application is incorporated by reference in its entirety.

BACKGROUND OF THE INVENTION

1. Field of the Invention

This invention relates generally to orthopaedic implants and, more particularly, orthopaedic implants having data acquisition capabilities.

2. Related Art

Trauma products, such as intramedullary (IM) nails, pins, rods, screws, plates and staples, have been used for many years in the field of orthopaedics for the repair of broken bones. These devices function well in most instances, and fracture healing occurs more predictably than if no implant is used. In some instances, however, improper installation, implant failure, infection or other conditions, such as patient non-compliance with prescribed post-operative treatment, may contribute to compromised healing of the fracture, as well as increased risk to the health of the patient.

Health care professionals currently use non-invasive methods, such as x-rays, to examine fracture healing progress and assess condition of implanted bone plates. However, x-rays may be inadequate for accurate diagnoses. They are costly, and repeated x-rays may be detrimental to the patient's and health care workers' health. In some cases, non-unions of fractures may go clinically undetected until implant failure. Moreover, x-rays may not be used to adequately diagnose soft tissue conditions or stress on the implant. In some instances, invasive procedures are required to diagnose implant failure early enough that appropriate remedial measures may be implemented.

The trauma fixation implants currently available on the market are passive devices because their primary function is to support the patient's weight with an appropriate amount of stability whilst the surrounding fractured bone heals. Current methods of assessing the healing process, for example radiography, patient testimonial, etc., do not provide physicians with sufficient information to adequately assess the progress of healing, particularly in the early stages of healing. X-ray images only show callus geometry and cannot access the mechanical properties of the consolidating bone. Therefore, it is impossible to quantify the load sharing between implant and bone during fracture healing from standard radiographs, CT, or MRI scans. Unfortunately, there is no in vivo data available quantifying the skeletal loads encountered during fracture healing as well as during different patient and physiotherapy activities. The clinician could use this information to counsel the patient on life-style changes or to prescribe therapeutic treatments if available. Continuous and accurate information from the implant during rehabilitation would help to optimize postoperative protocols for proper fracture healing and implant protection and add significant value in trauma therapy. Furthermore, improvements in security, geometry, and speed of fracture healing will lead to significant economic and social benefits. Therefore, an opportunity exists to augment the primary function of trauma implants to enhance the information available to clinicians.

Patient wellness before and after an intervention is paramount. Knowledge of the patient's condition can help the caregiver decide what form of treatment may be necessary given that the patient and caregiver are able to interact in an immediate fashion when necessary. Many times the caregiver does not know the status of a would-be or existing patient and, therefore, may only be able to provide information or incite after it was necessary. If given information earlier, the caregiver can act earlier. Further, the earlier information potentially allows a device to autonomously resolve issues or remotely perform the treatment based on a series of inputs.

Surgeons have historically found it difficult to assess the patient's bone healing status during follow up clinic visits. It would be beneficial if there was a device that allowed the health care provider and patient to monitor the healing cascade. Moreover, it would be beneficial if such a device could assist in developing custom care therapies and/or rehabilitation.

Additionally, surgeons have found it difficult to manage patient information. It would be beneficial if there was available a portable memory device that stored patient information, such as entire medical history files, fracture specifics, surgery performed, X-ray images, implant information, including manufacturer, size, material, etc. Further, it would be beneficial if such portable memory device could store comments/notes from a health care provider regarding patient check-ups and treatments given.

Therefore, there is a need in the art for an instrumented orthopaedic trauma implant that can provide precise and accurate information to doctors and patients concerning the status of the implant, progress of fracture healing, and the surrounding tissue without the need for x-rays or invasive procedures.

SUMMARY OF THE INVENTION

It is in view of the above problems that the present invention was developed. The invention is an instrumented orthopaedic implant, such as an intramedullary (IM) nail, with the capacity to provide an accurate measurement of the applied mechanical load across the implant. The implant includes sensors and associated electronic components for measurement of loads and transmission of the sensor data to an external reader.

One aspect of the invention is that it allows for information to be gathered and processed yielding conclusive valuable data with respect to a subject's bone healing cascade. The invention removes the guessing from the diagnosis by providing objective unbiased data collected from them throughout the healing process. Because the invention has a memory function, patient data can be stored; thus, allowing for the easy transmission of the data. The data may include personal data, patient history information, as well as patient activity. If the activity is captured, the surgeon could discern if the patient has been accurately performing postoperative rehabilitation regimens. This allows the surgeon to accurately predict and prescribe further regimens, which currently is not feasible with existing employed technology.

In another aspect of the invention, the captured information also can be used as an input to an algorithm that outputs a command for one or more reactions. The invention may react in a number of ways. The device enables the surgeon to allow autonomous intervention when needed to augment treatment using a biologic, such as injectable cements or demineralized bone matrix, to aid in the speed healing or informs the surgeon if a revision surgery may be necessary.

Thus, in furtherance of the above goals and advantages, the present invention is, briefly, a telemetric orthopaedic implant system, the system including an orthopaedic implant and a control unit. The orthopaedic implant includes at least one sensor; a first recess adapted to receive said at least one sensor; an electronic component electrically connected to said at least one sensor, the electronic component including at least a power supply, a first transmitter, a first receiver, and a first microprocessor; a second recess adapted to receive the electronic component; potting material to seal said first recess and said second recess; a power source electrically connected to said electronic component; and an acting unit electrically connected to said electronic component, said acting unit adapted to carry out a function based upon a condition. The control unit includes a second microprocessor; a second transmitter electrically connected to said second microprocessor, the second transmitter adapted to send a signal to said first receiver of said electronic component; and a second receiver electrically connected to said second microprocessor, the second receiver adapted to receive data from said first transmitter of said electronic component.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE EMBODIMENTS

Figure 1:
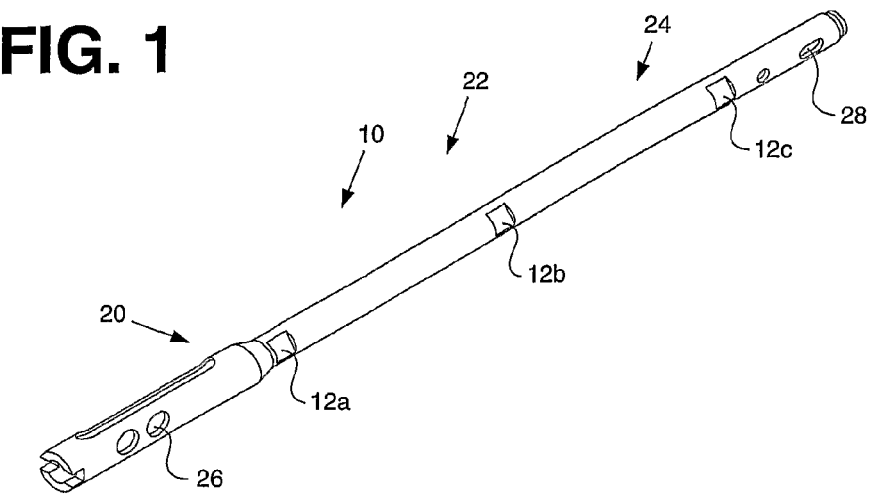
FIG. 1 is a perspective view of a telemetric orthopaedic implant in a first embodiment.
Figure 2:
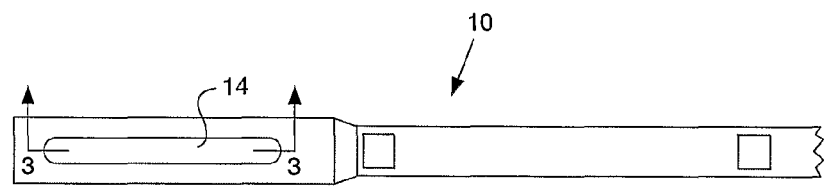
FIG. 2 is a top view of the implant shown in FIG. 1.
Figure 3:
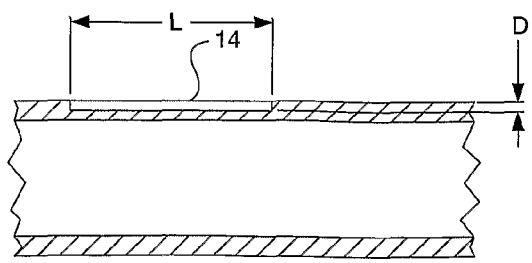
FIG. 3 is a partial sectional side view of the implant shown in FIG. 1.
Figure 4:
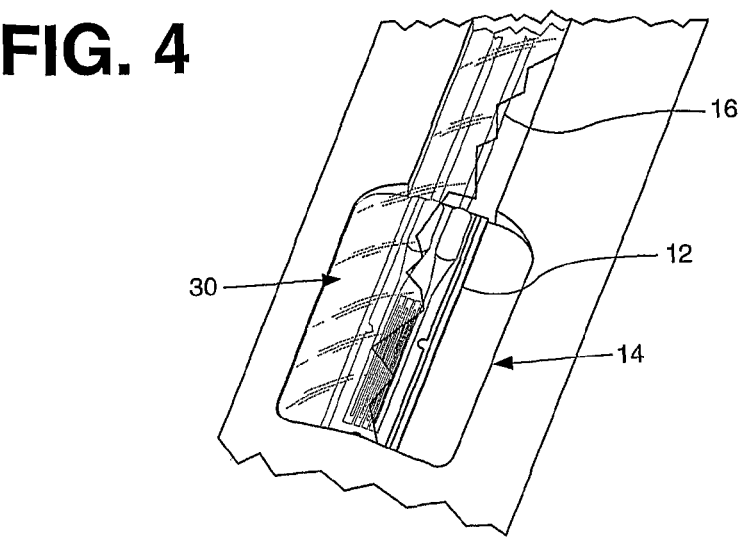
FIG. 4 is a detailed perspective view of the implant shown in FIG. 1.

A "smart implant" is an implant that is able to sense its environment, apply intelligence to determine whether action is required, and act on the sensed information to change something in a controlled, beneficial manner. One attractive application of smart implant technology is to measure loads on an orthopaedic implant. For example, an intramedullary nail is subjected to three types of loading: bending, torsional, and compression. These loads may be measured indirectly by measuring sensor output of a series of strain gauges mounted to the orthopaedic implant. In the case of an intramedullary nail, diametrically apposed strain gauges mounted on the outer surfaces of the nail are subjected to tensile and compressive forces, respectively. Typically, the strain measured from the sensors is higher when the implant is loaded in bending than in compression.

A fundamental parameter of the strain gauge is its sensitivity to strain, expressed quantitatively as the gauge factor (G). Gauge factor is defined as the ratio of fractional change in electrical resistance to the fractional change in length (strain), $$G = \frac{\Delta R}{R\varepsilon}, \tag{1}$$

where R=nominal resistance, ΔR=resulting change in resistance and ε=strain. This change in resistance arises from two important factors: (a) the change in the resistivity of the material, and (b) the change in the physical dimensions of the resistor as the material is deformed. For a foil strain gauge, G is found to be 2.1. Voltage recordings are converted to strain using the following equation:—

$$\varepsilon = \frac{-4V_r}{GF(1+2V_r)} x \left(1 + \frac{R_L}{R_g}\right), \tag{2}$$

where $R_L$ is the lead resistance, $R_g$ is the nominal gauge resistance, which is specified by the gauge manufacturer, GF is the Gauge Factor, which is also specified by the gauge manufacturer, and $V_r$ is the voltage ratio defined by the following equation:—

$$V_r = \left(\frac{V_{CH}(\text{strained}) - V_{CH}(\text{unstrained})}{V_{EX}}\right), \tag{3}$$

where $V_{CH}$ and $V_{EX}$ are the measured signal's voltage and excitation voltage respectively.

Strain is related to stress using Hooke's Law which can be rearranged to calculate the compression and bending loads experienced by the implant (F), $$E \cdot \varepsilon \cdot A = F \tag{4}$$

where E is the stiffness of the implant in gigapascals (GPa), $\epsilon$=strain measured from the output of the instrumented implant, and A is the cross-sectional area of the implant in square meters ($m^2$). The corresponding load on the bone could be deduced by subtracting the implant load from the total downward force exerted by the limb measured using either a force plate or a balance.

Incorporation of sensors and other electronic components within an implantable medical device, such as an intramedullary nail, alters its primary function from a passive load-supporting device to a smart "intelligent" system with the ability to record and monitor patient activity and compliance.

Telemetric Intramedullary Nail

Referring to the accompanying drawings in which like reference numbers indicate like elements, FIG. 1 illustrates a telemetric intramedullary (IM) nail 10. The telemetric IM nail 10 includes at least one sensor 12. One particular sensor configuration is illustrated in FIG. 1. In this embodiment, sensors 12 are located in a proximal region 20, a central or mid-shaft region 22, and a distal region 24 of the IM nail 10. In the embodiment depicted in FIG. 1, the telemetric IM nail 10 includes three sensors 12a, 12b, 12c with a sensor corresponding to each region. However, those of ordinary skill in the art would understand that a greater or lesser number of sensors may be used and that sensors may be applied in other configurations. The telemetric nail 10 continuously measures a set of strain values generated from the sensors 12. As explained in greater detail below, the telemetric IM nail 10 transmits the measurements from the nail to a reader device for calculation of the forces components without disturbing fracture healing.

The telemetric IM nail 10 may include features to allow fixation of the nail to bone. For example, the telemetric IM nail 10 may include proximal apertures 26 and/or distal apertures 28. In the embodiment depicted in FIG. 1, the telemetric IM nail 10 includes two proximal holes 26, a distal hole 28, and a distal slot 28, but those of ordinary skill in the art would understand that a greater or lesser number of apertures may be provided.

Figure 5:
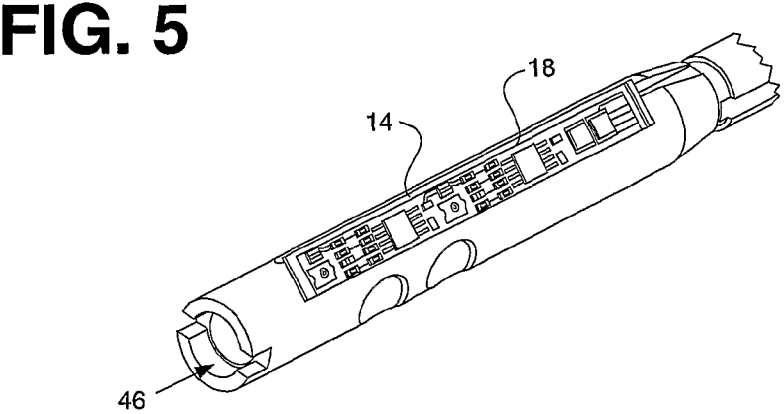
FIG. 5 is a perspective view of a telemetric orthopaedic implant in a second embodiment.

As best seen in FIG. 5, the telemetric IM nail 10 also includes one or more electronic components 18, such as a printed circuit board. The electronic components 18 form an instrumentation circuit with the sensors 12. The electronic components 18 may include associated signal conditioning circuitry, one or more microprocessors, one or more memory devices, a power supply, and communications components. The electronic components 18 allow in situ measurement of changes in the local environment. The combination of the sensor 12 and the electronic components 18 provide a powerful tool for indirect measurement of the changing load over time due to fracture consolidation using the algorithm described above. In turn, these indirect measurements may be used to provide information to clinicians on the environment for use in clinical decision making.

In order to maintain the integrity of the telemetric IM nail 10, the implant design must protect the components, provide an accurate and stable connection between the sensor and its environment, and maintain the functionality of the implant itself. Incorporating sensors within the structure of internal implants raises the "packaging problem" of maintaining the insulation of electronics, as biological tissues are an extremely hostile environment. Furthermore, the risk of damage to the electronic components 18 from common sterilization methods cannot be underestimated. Design considerations for instrumenting the IM nail 10 requires minimization of any damage to the mechanical and physical properties of the nail and allow for large scale commercialization and manufacture. Certain designs may be confirmed by measuring the bending stiffness and fatigue behavior of the IM nail 10 before and after instrumentation.

As best seen in FIGS. 2-5, the IM nail 10 includes at least one recess 14. As examples, the recess 14 may be rectangular, square, circular, elliptical, or some combination thereof. The recess 14 may be made using various manufacturing techniques including, but not limited to machining, milling, grinding, forging, casting, stamping, and injection molding. The recess 14 has a depth D, which ranges from about 0.1 mm to about 2.0 mm. The length L of the recess may be in the range from about 1 mm to about 100 mm. In the embodiment depicted in FIG. 3, the recess 14 is about 0.5 mm thick and about 5 mm long. The recess 14 receives the sensor 12 and conductor wires 16. The recess 14 protects the sensor 12 and conductor wires 16 from abrasive damage during the surgical insertion process. The recess 14 is located on either an anterior surface or a posterior surface enabling the sensors 12 to experience tensile and compression forces respectively. The sensor 12 may be fixed in the recess 14 using a range of high stiffness adhesives including epoxy resins, polyurethanes, UV curable adhesives, and medical grade cyanoacrylates. These types of fixation methods do not adversely affect the performance of the sensor 12.

Additionally, the telemetric IM nail 10 may include a recess 14 in the proximal region 20 to receive the electronic components 18. The recess 14 is dimensioned to accept the electronic components 18. For example, the electronic components may be about 56 mm long, about 6.2 mm wide, and about 0.25 mm thick, and the recess 14 is sized accordingly. The recess 14 may be of the same size as the electronic components 18 or slightly larger.

Alternatively, installation of the strain gauges 12 and other electronic components may be carried out using a more evasive method, such as electro-discharge milling a longitudinal section in the implant, installing the components in the IM nail 10, and laser welding the tube segments. However, there are several disadvantages to using this approach. Localized heat of welding tends to cause distortion and warping of the base metals or stresses around the weld area, which could affect the corrosion resistance of the implant. Moreover, laser beam welding has a tremendous temperature differential between the molten metal and the base metal immediately adjacent to the weld. Heating and cooling rates are much higher in laser beam welding than in arc welding, and the heat-affected zones are much smaller. Rapid cooling rates can create problems such as cracking in high carbon steels.

There are a number of ways to encapsulate the sensors 12 and other electronic components. Some components may require more durable methods of encapsulation than others. For example, if a battery or other potentially hazardous device is included in the electronics system a titanium case may be required. Alternatively, if the components are biologically benign, then a simple potting material, such as polyurethane or a silicone, may prove to be sufficient. Those skilled in the art would understand that various materials may be used for the potting material. What is significant is that the potting material acts as a cover to separate the electronic components from the surrounding environment. Soldering and welding techniques may also be used to help permanently seal the sensors 12 and other electronic components inside the instrumented nail 10. Substituting the standard foil gauge with platinum strain gauges may also enhance durability and resistance to sterilization and attack by biological fluids.

Figure 6:
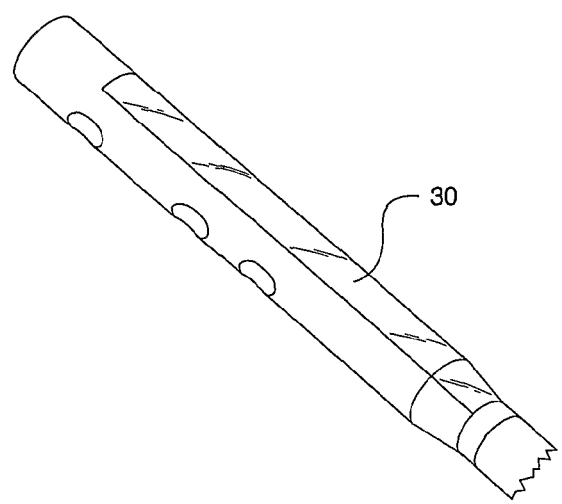
FIG. 6 is a perspective view of the telemetric orthopaedic implant shown in FIG. 5.

In one particular embodiment in FIG. 6, the sensors 12 and the electronic components 18 are covered with a biocompatible potting material 30, such as polyurethane or silicone, in order to provide a hermetic seal. Because the sensors 12 and the electronic components 18 are sealed hermetically from the patient tissues and fluids, long term function of the telemetric IM nail 10 is achievable. At the same time, leakage of non-biocompatible or toxic materials is eliminated. The potting material 30 is an electrically insulative, moisture resistant material, supplied in either a liquid or putty-like form and is used as a protective coating on sensitive areas of electrical and electronic equipment. The potting material 30 may be optically opaque or colorless. The strain gauges 12 and conductor wires 16 are covered in potting material 30 with suitable mechanical characteristics required to survive the implantation process and restore the mechanical envelope.

Figure 7:
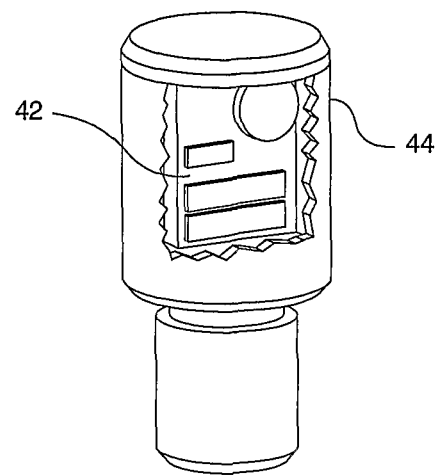
FIG. 7 is a perspective view of an insert.
Figure 8:
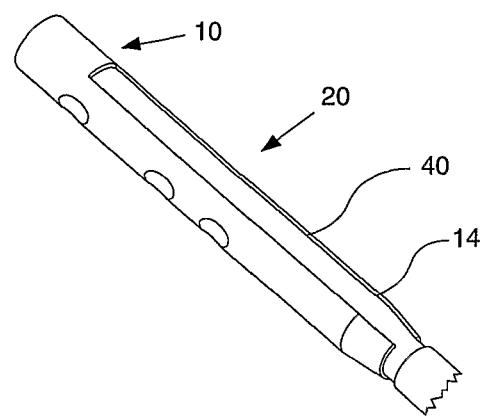
FIG. 8 is a perspective view of a telemetric orthopaedic implant in a third embodiment.
Figure 9:
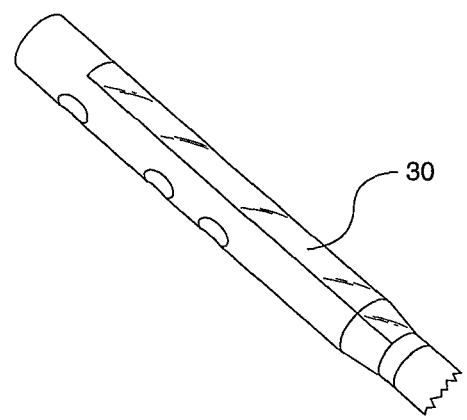
FIG. 9 is a perspective view of the telemetric orthopaedic implant shown in FIG. 8.

An alternative arrangement of the electronic components 18 in the telemetric instrumented nail 10 is shown in FIGS. 7, 8, and 9. In this particular design, passive electronic components 40 are located in the recess 14 of the proximal region 20 and active electronic components 42, such as a power supply, microprocessor, data storage device, and external communication device, are contained in a separate nail head insert 44. As best seen in FIG. 9, the passive electronic components 40 may be covered with the potting material 30 to hermetically seal the electronic components 40. In this configuration, the telemetric IM nail 10 is implanted in the usual manner, and, once the nail has been implanted into the bone, the nail head insert 44 is attached to the telemetric IM nail 10. For example, the nail head insert 44 may be threaded into a hole 46 (best seen in FIG. 5). This particular design avoids any sensitive electronics being damaged by the implantation process. Connections between the passive and active electronic components 40, 42 can be made using either an inductively coupled link or physical connections via slip rings.

The telemetric IM nail 10 may be constructed from a biocompatible material using standard manufacturing techniques. For example, the nail may be forged out of metal, hand or machine laid composite, or machined from stock. Alternatively, the telemetric IM nail 10 may be cast, injection molded, or compacted through hot isostatic processing (HIP). The HIP manufacturing process is particularly suited for producing nails with preformed recesses designed to receive sensors and electronic components.

In yet another alternative embodiment, the telemetric IM nail 10 may be constructed using a biodegradable composite whose degradation rate is controlled by sensed strain data. Such a device is more compliant than a conventional metal implant because the mechanical modulus of the implant changes according to the degree of healing of the adjacent bone. Increased load bearing capacity on the healing bone triggers the release of an active agent that accelerates the degradation rate of the nail in order to reduce its load sharing ability. On the other hand, slow healers require the release of active agents that inhibit the degradation rate of the implant material. The release of the active agent may be controlled using a micro-electromechanical structures (MEMS) reservoir system that releases a chemical manipulation on demand that either accelerates or decelerates the rate of degradation of the nail. The instrumented components may be manufactured using restorable materials, such as degradable, porous silicon wafers. Otherwise, non-degradable electronic components may remain in the patient, which may be acceptable in some cases.

FE Modeling to Determine Optimum Position of Sensors

Figure 10:
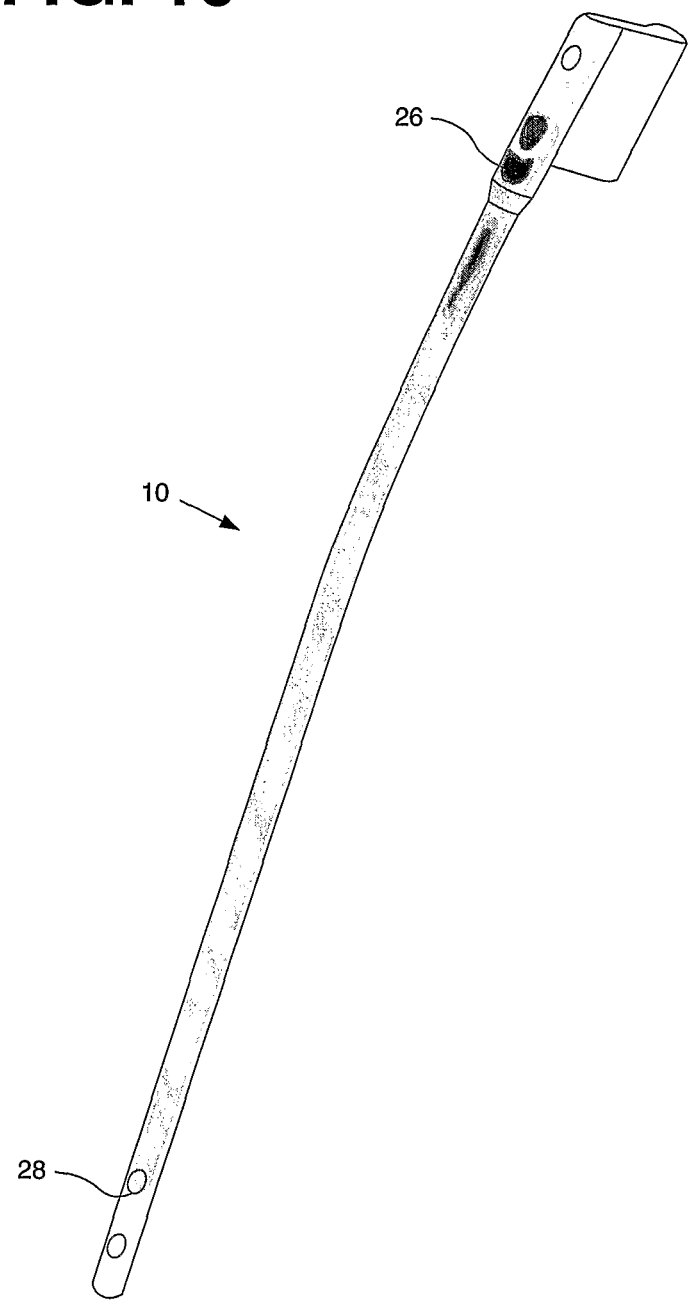
FIG. 10 is a perspective view of a telemetric orthopaedic implant illustrating the results of finite element analysis.

Referring now to FIG. 10, the sensors 12 may be devices capable of measuring mechanical strain, such as foil or semiconductor strain gauges. Alternatively, the sensors 12 may be load cells used to directly measure mechanical load. The embodiment depicted in FIG. 1 utilizes foil strain gauges to measure strain. The optimum location of the sensors 12 for the purpose of measuring strain may be determined through finite element (FE) analysis. The sensors 12 may be located, for example, but not limited to, in the working region of the implant 10. The working region is defined as the region between two fixation apertures 26, 28. The fixation apertures 26, 28 are adapted to receive fasteners, such as screws, to attach the implant 10 to bone. As can be seen in FIG. 10, the darker, shaded areas represent stress concentrations. The stress distribution results from the way in which the nail 10 is loaded through the patient's hip joint and results in high bending stresses on the outer surface of the nail 10, aligned with the proximal apertures 26. Typically, a 50% reduction in stress is observed between sensors placed inside the implant as opposed to an external mounting.

Sensor

The telemetric IM nail 10 includes the sensor 12. The sensor 12 senses at least one item, event, condition, etc. The sensor 12 may be any number of types including, but not limited to, a foil strain gauge, a semi-conductor strain gauge, a vibrating beam sensor, a force sensor, a piezoelectric element, a fibre Bragg grating, a gyrocompass, or a giant magneto-impedance (GMI) sensor. Further, the sensor 12 may indicate any kind of condition including, but not limited to, strain, pH, temperature, pressure, displacement, flow, acceleration, direction, acoustic emissions, voltage, pulse, biomarker indications, such as a specific protein indications, chemical presence, such as by an oxygen detector, by an oxygen potential detector, or by a carbon dioxide detector, a metabolic activity, or biologic indications to indicate the presence of white blood cells, red blood cell, platelets, growth factors, or collagens. Finally, the sensor 12 may be an image capturing device.

Some orthopaedic applications may require more than one sensor to measure more than one item, event, or condition. Thus, some implants require multi-channel capabilities. For example, the telemetric IM nail 10 may include six or more strain gauges. The sensor 12 may be an array of sensors or a series of discrete sensors. The telemetric IM nail 10 also may be designed with multiaxial strain gauges in a rosette configuration to enable loads to be measured in x, y and/or z planes. The configuration of the sensors 12 also may be tailored to meet the requirements of the patients fracture. The sensor 12 is designed in such way that it does not compromise the performance of the implant. For example, the sensor 12 must be unobtrusive, biocompatible, and in no way affect the established biomechanical performance of the implant. It has been shown that nails with a tight fit between implant and the adjacent bone may be deformed significantly during insertion. As a result, the resolution of the selected sensor is better than 8 bit (0.05%). The output of the sensor may be investigated by applying an axial load to the instrumented nail.

Figure 11:
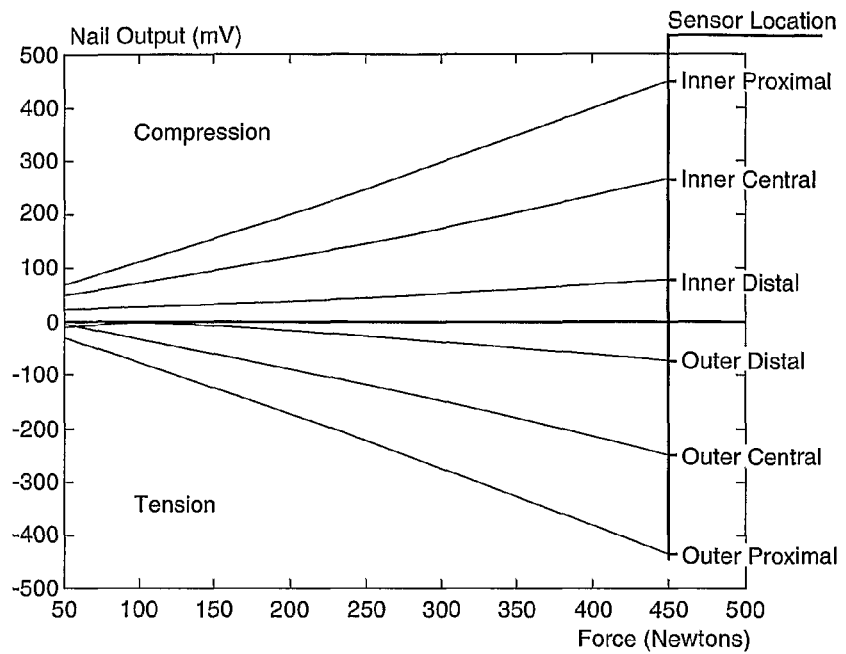
FIG. 11 is a graph illustrating data output vs. force.

The loading configuration is designed to match the loading pattern typically observed in a human femur, i.e. an offset vertical load transmitted through the nail via the proximal fastener. Strain vs. load plots for three instrumented IM nails with two strain sensors 12 located on the inner (compression) and outer (tensile) surfaces at either the mid-shaft region (nail 1), distal region (nail 2), or proximal region (nail 3) respectively are shown in FIG. 11. In all cases, the responses from the sensor pairs are fairly linear when the load on the nail is ramped up to 500 N. In addition, there is little or no hysteresis observed when the load is applied and removed from the nail.

Communication

The electronic components 18 are in communication with a data receiver 50. The electronic components 18 receive data from the sensor 12 and transmit the data to the data receiver 50. The electronic components 18 transmit the data by wire or through a wireless connection. The transmission may use available technologies, such as ZIGBEE™, BLUETOOTH™, Matrix technology developed by The Technology Partnership Plc. (TTP), or other Radio Frequency (RF) technology. ZigBee is a published specification set of high level communication protocols designed for wireless personal area networks (WPANs). The ZIGBEE trademark is owned by ZigBee Alliance Corp., 2400 Camino Ramon, Suite 375, San Ramon, Calif., U.S.A. 94583. Bluetooth is a technical industry standard that facilitates short range communication between wireless devices. The BLUETOOTH trademark is owned by Bluetooth Sig, Inc., 500 108th Avenue NE, Suite 250, Bellevue Wash., U.S.A. 98004. RF is a wireless communication technology using electromagnetic waves to transmit and receive data using a signal above approximately 0.1 MHz in frequency. Due to size and power consumption constraints, the telemetric IM nail 10 may utilize the Medical Implantable Communications Service (MICS) in order to meet certain international standards for communication.

Instrumentation System

Figure 12:
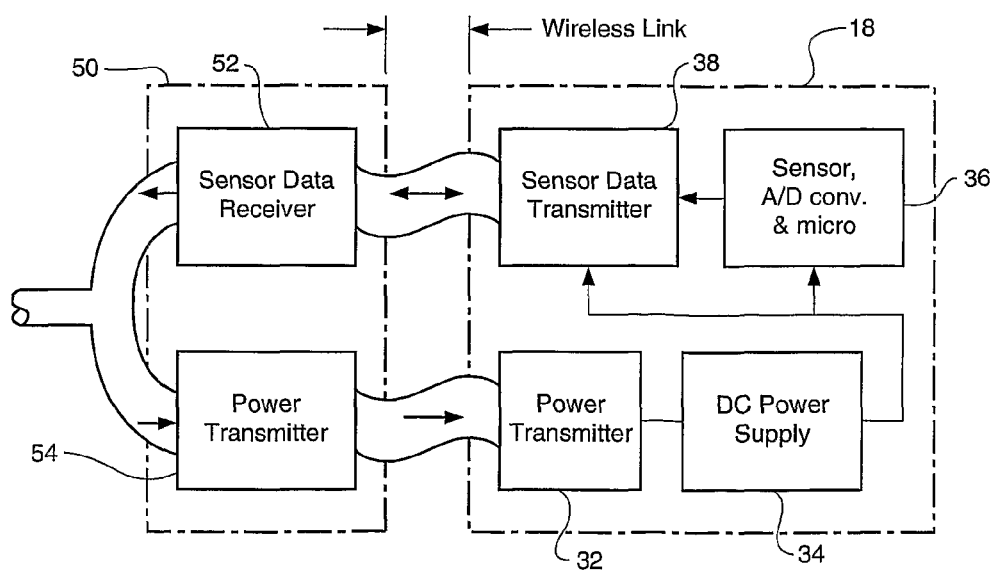
FIG. 12 is a schematic illustrating an electronic component and a data receiver.

FIG. 12 illustrates the electronic components 18, such as a printed circuit board, and the data receiver 50. The electronic component 18 includes a power transmitter 32, a DC power supply 34, a combination analog/digital converter and microprocessor 36, and a sensor data transmitter 38. The data receiver 50 includes a sensor data receiver 52 and a power transmitter 54. Although illustrated as separate components, those of ordinary skill in the art would understand that the transmitter and the receiver may be combined in a single unit, sometimes referred to as a transceiver. In the embodiment depicted in FIG. 12, power consumption and data transmission are contactless. The electronic component 18 may include any of the following: (1) any number of foil strain gauges; (2) matching number of low noise, low power instrumentation amplifiers; (3) matching number of Wheatstone bridge resistor networks; (4) matching number of strain gauge zero-adjustments; and (5) on-board power supply with noise filtering.

Power Management

The telemetric IM nail 10 may incorporate one or more power management strategies. Power management strategies may include implanted power sources or inductive power sources. Implanted power sources may be something simple, such as a battery, or something more complex, such as energy scavenging devices. Energy scavenging devices may include motion powered piezoelectric or electromagnetic generators and associated charge storage devices. Inductive power sources include inductive coupling systems and Radio Frequency (RF) electromagnetic fields.

Finally, the telemetric IM nail 10 may incorporate a storage device (not shown). The storage device may be charged by an inductive/RF coupling or by an internal energy scavenging device. The storage device must have sufficient capacity to store enough energy at least to perform a single shot measurement and to subsequently process and communicate the result.

Figure 13:
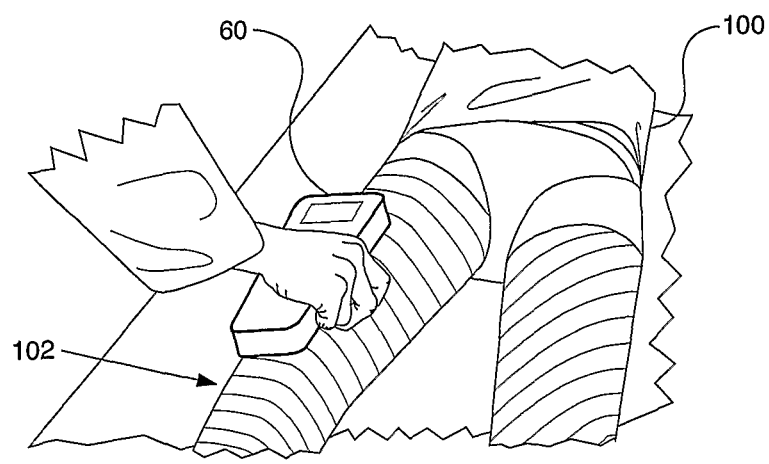
FIG. 13 illustrates use of a handheld device.
Figure 14:
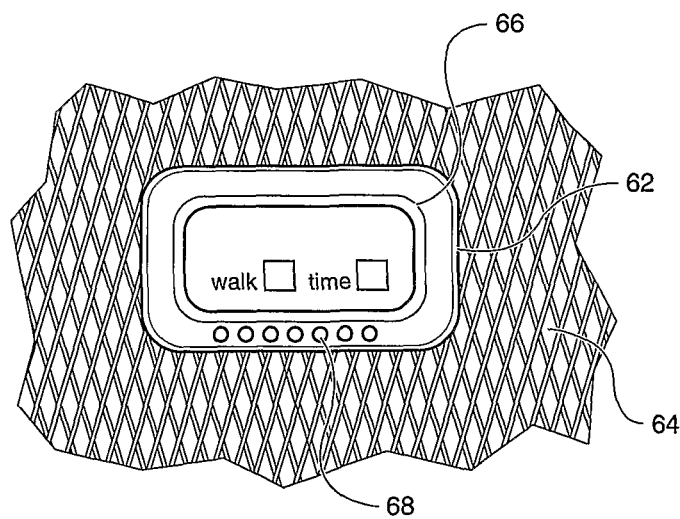
FIG. 14 illustrates a control unit.

FIG. 13 illustrates a handheld device 60 being placed on a leg 102 of a patient 100. The handheld device 60 generates RF waves that excite the electronic component 18. The excited electronic component 18 retrieves stored sensor readings and sends them to the handheld device 60 via a carrier wave. The handheld device 60 may be equipped with a processor (not shown) for direct analysis of the sensor readings or the handheld device 60 may be connected to a computer for analysis of the sensor readings.

Communication

The demands on an implantable telemetry system are severe and robust methods must be utilized to capture data from the orthopaedic implant. Prior attempts in the art have not provided a signal in the range needed for an instrumented intramedullary nail. Thus, the telemetric IM nail 10 has a wired interface in its most simplified version. In other words, the electronic components 18 are connected to an external control unit 62 via a wire (not shown). The control unit 62 may be placed on the patient 100 as a wearable device, such as an arm band, wrist band, thigh band, or anklet bracelet. Alternatively, the control unit 62 may be connected to a cast 64, such as by placing the control unit inside the cast or attaching the control unit to the exterior of the cast.

The control unit 62 may include a display 66 and/or a speaker 68. The display 66 may be used to display sensor readings, provide warning lights, a count down timer allowing the patient to anticipate an important event, such as cast removal, or an entertainment device, such as an electronic game, to occupy time. The speaker 68 may be used to provide sounds, such as pre-recorded instruction, warning sounds, or game sounds.

The patient actively wears the control unit 62 which constantly monitors the patient's activity. In the case of a major event, such as a traumatic incident or loss of essential body function, the control unit 62 senses this change and sends out an alert which could be audible and/or visual. Alternatively or in addition to the alert, the control unit 62 may send information to another device which could prompt the wearer for information to confirm the patient's status. The control unit 62 could also be used to notify emergency assistance groups of impending danger and other pertinent information, such as location of the patient. In this last example, the control unit 62 may include a global positioning system (GPS) module to locate the control unit and patient.

The control unit 62 may be housed in virtually any type of material, such as plastic, rubber, metal, glass, ceramic, wood, stone, long fiber composites, short fiber composites, non-fiber composites, etc. The display 66 may be a liquid crystal display, a light emitting diode display, a plasma display, a digital light processing, a liquid crystal on silicon display, cathode ray tube, etc.

In other embodiments, however, the telemetric IM nail 10 has a wireless communications facility to allow the patient to move around freely. This embodiment is partially depicted in FIG. 12.

Figure 15:
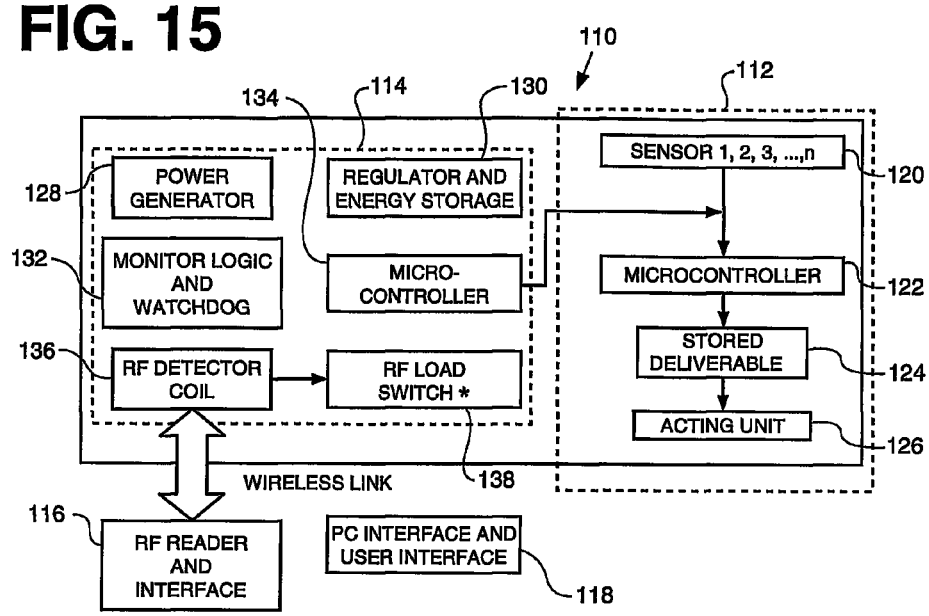
FIG. 15 is a schematic illustrating a telemetric orthopaedic implant system.

Not only does the telemetric IM nail 10 include a sensor, but also the telemetric IM nail may include an acting unit to perform certain functions based on sensor readings or external commands. FIG. 15 illustrates a telemetric implant system 110. The telemetric implant system 110 includes a telemetric orthopaedic implant 112, a control unit 114, a reader 116, and a computing device 118. The reader 116 wirelessly communicates with the control unit 114 to transmit and receive data. The reader 116 is connected to the computing device 118 either by wires or wirelessly. The computing device 118 may be any number of known devices, such as a personal digital assistant, a desktop computer, a laptop computer, a notepad PC, a biometric monitoring device, a handheld computer, or a server. The computing device 118 is used to analyze the data received from the orthopaedic implant 112. The computing device 118 may be used to store data and/or to program the telemetric orthopaedic implant 112. The reader 116 and the computing device 118 may be incorporated into a single device.

The orthopaedic implant 112 includes one or more sensors 120, a microcontroller 122, one or more stored deliverables 124, and one or more acting units 126. The sensor 120 outputs an induced signal to a preamplifier (not shown), then to an amplifier (not shown), and then to a filter (not shown). The signal travels then to the microcontroller 122 which processes the sensor signal via an algorithm and decides if the information is to be stored or sent to the acting unit 126. The algorithm used to decide how to act can be pre-programmed from the manufacturer or by surgeon preference. The acting unit 126 may communicate with the microcontroller 122 either by wire or wirelessly. Upon receiving the signal from the control unit 114 or the microcontroller 122, the acting unit 126 deploys a stored deliverable 124, which includes, but is not limited to, biological manipulations, an antibiotic, an anti-inflammatory agent, a pain medication, an osteogenic factor, radio-markers, angiogenic factors, vasodilator, and/or growth factors.

The acting unit 126 may be a MEMS device, such as a pump that delivers a specific volume of medicament or other stored deliverable 124. The orthopaedic implant 112 may include several of these pumps that all contain the same stored deliverable 124 as to offer redundancy in case one or more of the pumps fail. The pump contains a reservoir or reservoirs of stored deliverable 124 to be delivered. The stored deliverable 124 is delivered using any type of microfluidic mechanism, such as a rotary pump, a piston pump, a shape memory material pump, etc.

The control unit 114 includes a power generator 128, an energy storage device 130, a logic circuit 132, a microcontroller 134, an RF detector coil 136, and an RF load switch 138.

User Interface

In some embodiments, the computing device 118 includes a graphical user interface (GUI). The GUI allows a healthcare provider and/or patient to display information based on the collected data either locally or remotely, for example telemedicine, from the telemetric orthopaedic implant 112. The GUI identifies the system to communicate with, prompts the user for security clearance, verifies the security clearance, and downloads the data from the telemetric orthopaedic implant 112 or the reader 116. The data could then be further processed into various forms from simple discrete healing progress status numbers or verbiage to complex information such as a graphical reproduction of the patient gait cycle curve, patient activity, patient compliance, patient data, healthcare provider information, implant manufacture information, surgical techniques, x-radiograph information, computed tomography imaging information, magnetic resonance imaging information.

Further, the patient could be alerted by the GUI as a result of sensed information. The logic circuit 132 may be used to monitor data received from the telemetric orthopaedic implant 112 and send a signal if a certain variable exceeds a preconfigured limit. The alert could let the user know when a clinic visit is necessary for doctor intervention, the device has been overloaded, or how to manage a situation that has occurred without surgeon intervention.

The telemetric implant system 110 has many uses. For example, a patient may undergo a surgical intervention to repair a sustained injury or joint reconstruction, during which time the patient receives a telemetric orthopaedic implant to aid in the repair of the injury. The implant may utilize an electromechanical system designed to monitor various aspects of the patient's recovery with one or more sensors, decide if an action needs to take place, and hence act as programmed.

Early Monitoring of Bone Healing

While immobilization and surgery may facilitate bone healing, the healing of a fracture still requires adequate physiological healing which can be achieved through continuously monitoring changes in the in situ load distribution between the implant and the surrounding bone using sensors and a biotelemetry system. The mass and architecture of bone are known to be influenced by mechanical loading applied to them. In the absence of appropriate loading due to stress shielding caused by poor management of internal orthopaedic fixation systems, bone mass is reduced resulting in compromised healing of the fracture. The primary function of an telemetric orthopaedic implant is to carry the load immediately after surgical placement. For example, the telemetric orthopaedic nail carries the load immediately after surgical placement in the intramedullary canal. With progression of fracture healing, the load sharing between the implant and the bone changes. This can be tracked using strain gauges optimally positioned within the orthopaedic implant according to the location of the fracture. The sensors are used to monitor the progress of union in the case of fracture by continuously monitoring the load component of the healing bone in all spatial components, which is unobtainable from X-rays. Periodic follow-up will provide a graph that shows the gradual decrease of relative motion of the fragments until union occurs.

Each fracture patient generates his or her own unique healing curve; however, the general shape of the healing curve indicates whether the fracture will progress to either a union condition or a non-union condition. The healing curve generated from a patient is dependent upon a number of factors including the type and location of the fracture, health status (underlying disease), age, activity, rehabilitation, and time to reach weight bearing.

Figure 16:
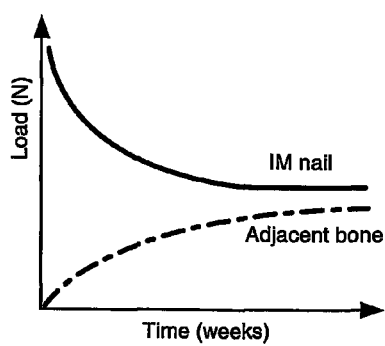
FIG. 16 is a graph illustrating a fracture healing curve.
Figure 17:
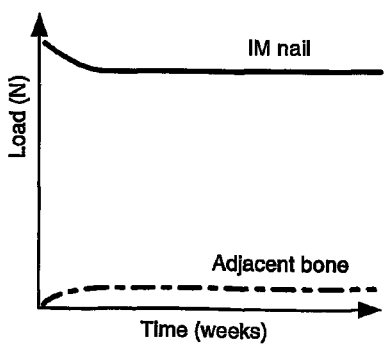
FIG. 17 is a graph illustrating a non-union fracture healing curve.

Hypothetical load vs. healing time curves showing the loading distribution between an instrumented IM nail and the surrounding bone are schematically illustrated in FIG. 16 and FIG. 17. In FIG. 16, the fracture is progressing to a union condition, and in FIG. 17, the fracture maintains a non-union condition. Although fracture healing results in a reduction in implant load, the remaining load of the nail can be significant and are expected to increase with patient activity. It has been suggested that loading of the bone may increase up to 50% after implant removal. The load measured in the adjacent bone can be determined by subtracting the implant load from the load exerted through the limb, which is determined using either a force plate or balance. The clinician can also measure the load acting through the contralateral limb in order to provide a reference measurement for a fully functional limb.

The healing curve may be used in several different ways. First, in the case of an active telemetric orthopaedic implant, the implant or control unit continuously records data. In the case of an intramedullary nail as an example, the strain on the implant is recorded as the patient ambulates. The surgeon or other healthcare provider may download the data from the implant or control unit in a clinical setting. The data is processed and a healing curve is generated from the data. If the surgeon observes that the strain on the implant is decreasing with time, similar to the graph of FIG. 16, this implies that the surrounding hard tissue is accepting some of the load and, thus, the fracture is healing. However, if the strain on the implant is unchanged with time and at the approximate level as when the patient was discharged from the hospital or other health care facility, similar to the graph of FIG. 17, then this implies that the surrounding hard tissue is not bearing the load and, therefore, the fracture is not healing.

Second, the telemetric orthopaedic implant may be a passive device that does not record data continuously but only when it is exposed to an energy source. In this embodiment, the hospital or healthcare facility provides an energy source which energizes the telemetric orthopaedic implant and allows it to record data. In this example, the telemetric orthopaedic implant is energized, a load is placed on the affected bone with the implant at to a set level, and sensor readings are captured. For example, the implant may be an intramedullary nail and the sensors may measure strain on the nail as the load is applied. The sensed data is downloaded and processed. In this example, the sensed data must be compared to previous measurements. For example, measurements may be taken at predetermined time periods, such as daily or weekly. If the load applied to the bone is unchanged and the strain has decreased compared to previous measurements over time, then it is implied that the hard tissue is sharing some of the load and, thus, the fracture is healing. However, if the strain on the implant remains unchanged compared to previous measurements over time, this implies that the surrounding hard tissues is not bearing any of the load and, therefore, the fracture is not healing.

Telemetric orthopaedic implants of the kind described herein utilize an algorithm that gives an early indication as to whether the fracture will heal or not based on the rate of change in the initial load measurements. The information provided by the sensors also may be used to design a new class of orthopaedic implants that are more compliant with the surrounding bone in terms of strength and stiffness.

Figure 18:
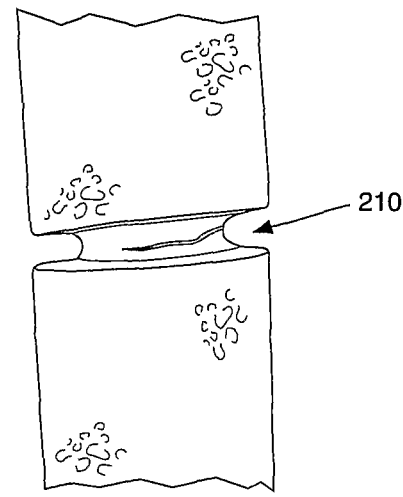
FIG. 18 illustrates an artificial fracture gap.
Figure 19:
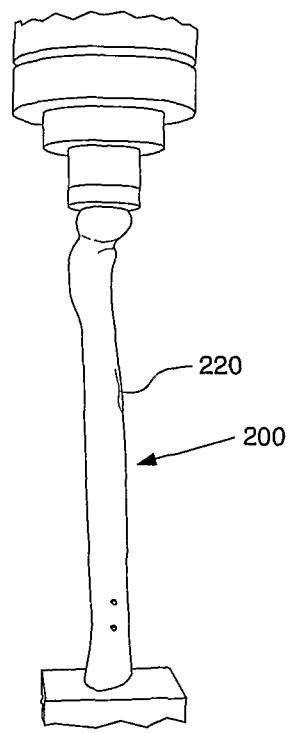
FIG. 19 illustrates an in vitro biomechanical test setup.

The functionality of a telemetric orthopaedic implant may be demonstrated in vitro using a plastic fracture model. In this test shown in FIGS. 18 and 19, a telemetric intramedullary nail 220 is implanted in an intact femur model 200 and gradually, a circumferential fracture gap 210 is introduced while observing changes in the strain as a function of load. Thus, reversing the fracture conditions typically observed in vivo. The strain gauges are applied to the medial and lateral sides of the nail 220, positioned on the shaft of the nail to correspond with the fracture gap placement. Interpretation of the data obtained from this study represents the ability to measure bone healing in vivo. The nail construct is loaded at a stepwise displacement from 0 lbf to 300 lbf in predetermined increments and the strain is measured at each load increment. The first series of strain measurements are made with the bone model completely intact. The next series of strain measurements are made with 75% of the fracture gap 210 in place. Subsequently, the third, fourth, and fifth series of strain measurements are made with 50%, 25%, and 0% of the fracture gap 210 in place, respectively. A final series of strain measurements is made with the fracture gap segments re-inserted to their original position. The fracture gap 210 is approximately 5 mm thick, positioned on the shaft of the bone model such that it will be at half of the working distance of the nail 200, which means it is half of the distance between the locking fasteners.

Figure 20:
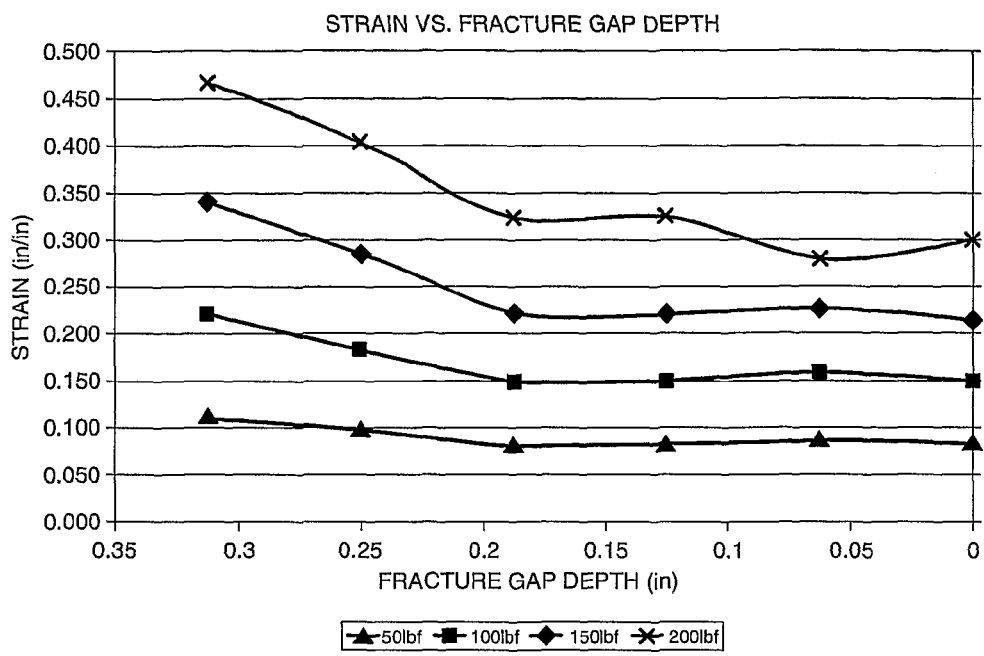
FIG. 20 is a graph illustrating strain vs. fracture gap depth as a function of load.
Figure 21:
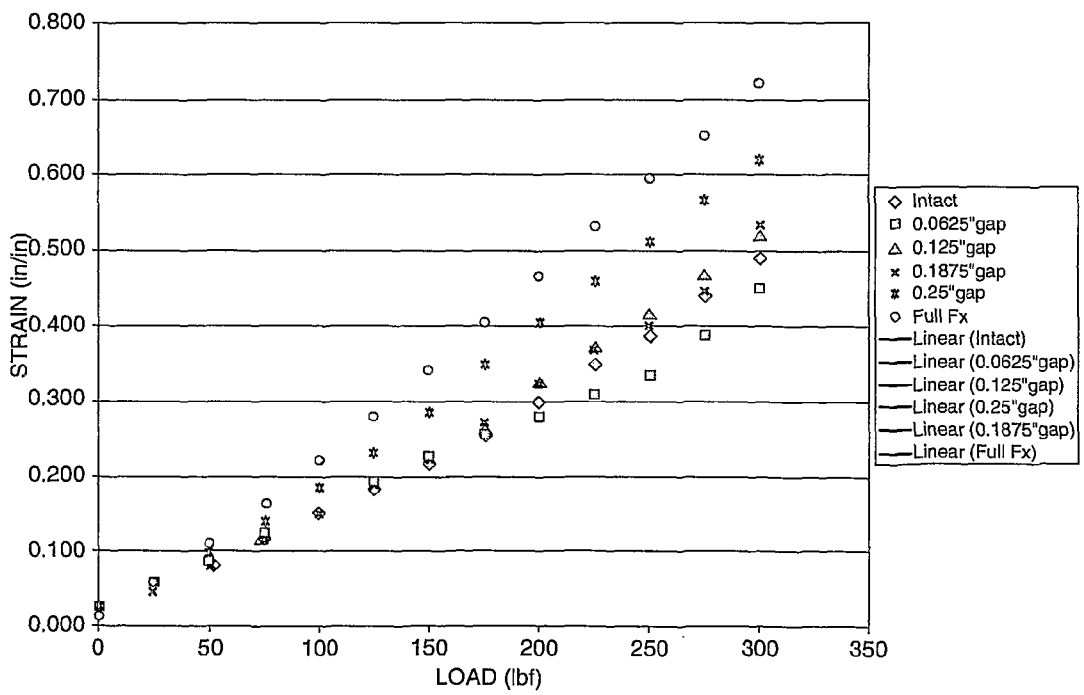
FIG. 21 is a graph illustrating strain vs. load as function of gap volume.

FIG. 20 illustrates reverse simulated bone healing using an artificially induced circumferential gap. FIG. 21 illustrates load vs. strain curves obtained from the plastic fracture model with 100% (fully intact), 75%, 50%, 25%, and 0% (fully fractured) of the fracture gap in place.

Gait Analysis

Figure 22:
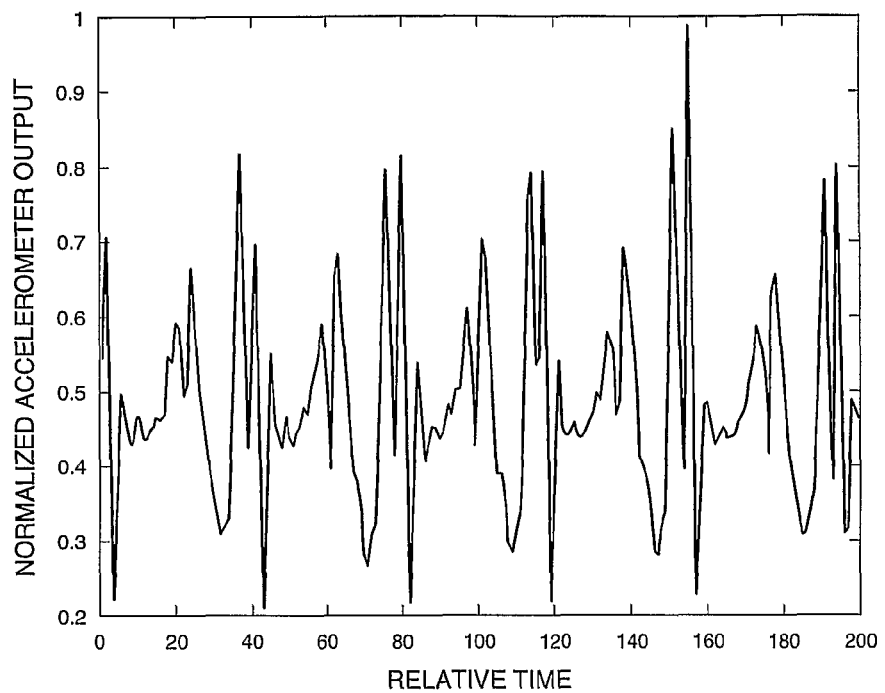
FIG. 22 is a graph illustrating accelerometer output vs. time.
Figure 23:
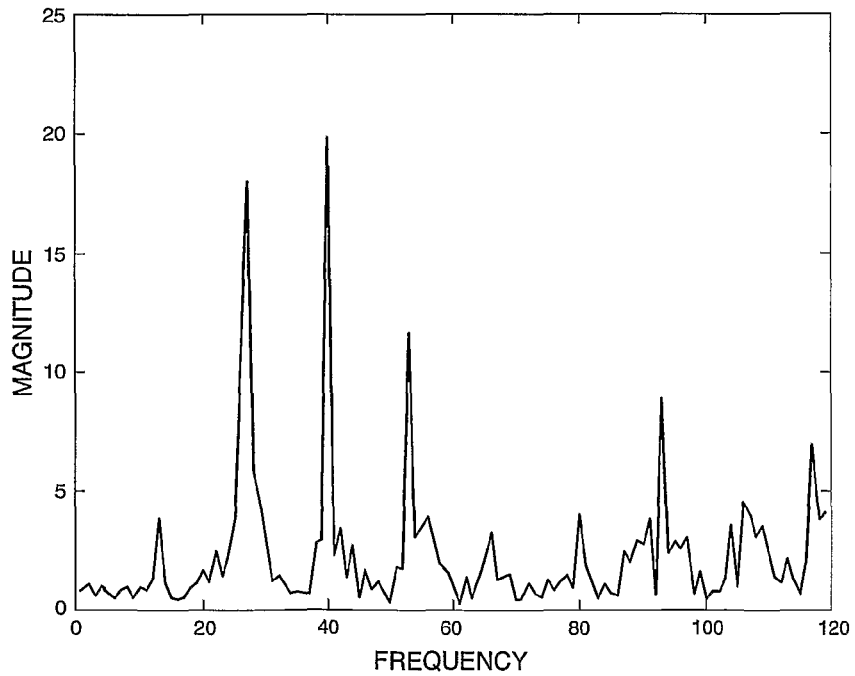
FIG. 23 is a graph illustrating magnitude vs. frequency.
Figure 24:
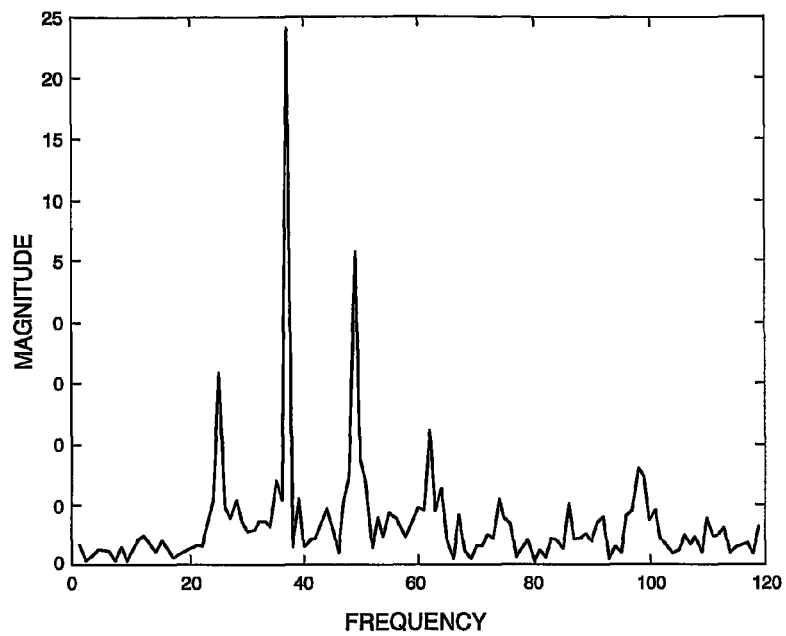
FIG. 24 is a graph illustrating magnitude vs. frequency.
Figure 25:
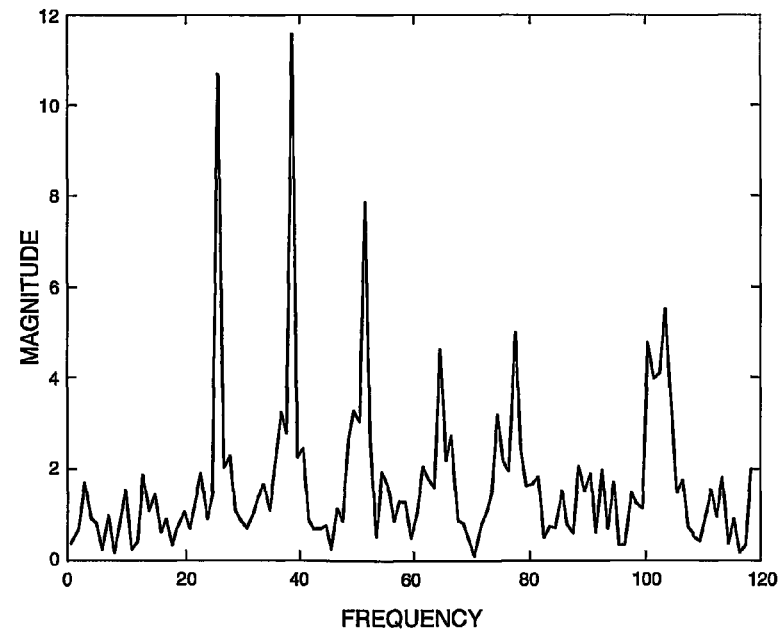
FIG. 25 is a graph illustrating magnitude vs. frequency.
Figure 26:
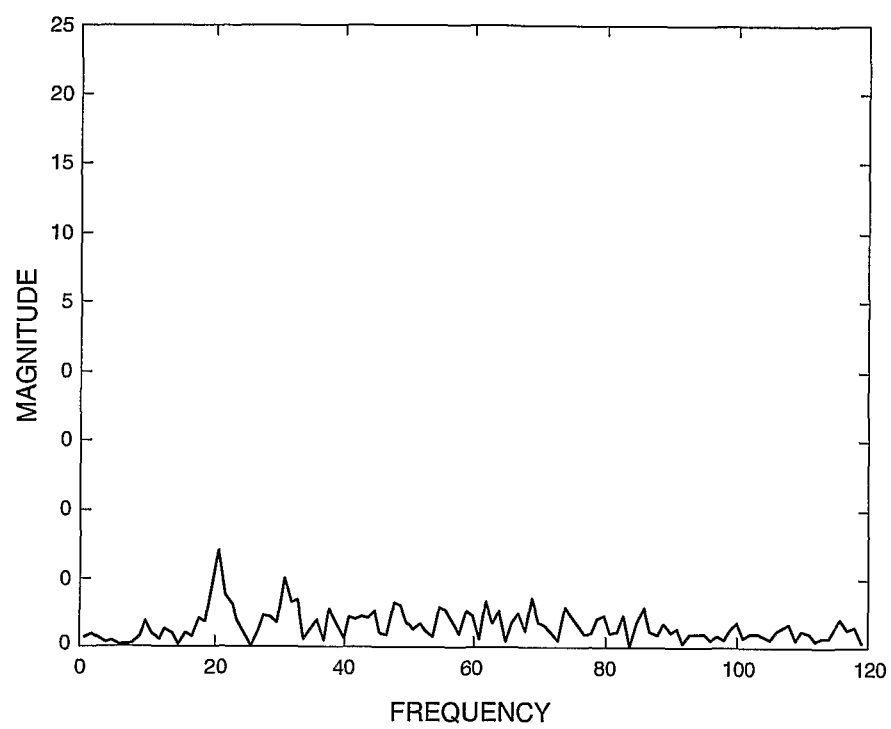
FIG. 26 is a graph illustrating magnitude vs. frequency.

The invention also includes a gait analysis tool in which gait data is gathered, processed, and stored until an external device accesses the data and presents it to a reviewer, such as a patient, surgeon, healthcare provider, or physical therapist. The telemetric orthopaedic implant may include an accelerometer, which can output acceleration changes over time at a sampling rate ranging from about 1 to about 2000 Hz. Reference FIG. 22 for an example of graphically represented data output resulting from wearing an accelerometer and the wearer undergoing normal unassisted gait. The sensor output data can then be manipulated as desired for analysis. One such method is to convert the data from the time domain to the frequency domain and look for biometric markers or patterns. FIGS. 23-25 show data similar to that in FIG. 22 transformed into the frequency domain. In these figures, distinct peaks are seen at various frequencies which define the wearer's gait signature seen as the differences in FIGS. 23-25. The patient's gait changes gradually with time and aging or abruptly as would be the case when a patient sustains a severe traumatic injury to any of the bone in their lower extremity. The frequency domain gait signature for an artificially induced antalgic gait pattern is seen in FIG. 26.

The gait analysis tool allows for basic information to be gathered and processed yielding conclusive valuable data with respect to a subject's gait cycle. This data can be used to diagnose the patient's healing status in at least their lower extremities, which when injured impede the normal gait cycle. Historically, surgeons have had to rely on radiographs or other imaging techniques to determine the stage of the patient's bone healing cascade. These tools are helpful but allow for error in diagnosis. There are several areas for this opportunity including but not limited to image quality, parallax, and misdiagnosis. Further, even though these diagnosis tools exist, the surgeon relies on patient testimonial more heavily than the images. The gait analysis tool removes the guessing from the diagnosis by providing the surgeon objective unbiased data collected from the patient throughout the healing process. The gait analysis tool allows the surgeon to understand earlier in the healing process if intervention is needed to augment treatment using a biologic, such as an injectable cement or demineralized bone matrix, to speed healing or if a revision surgery may be necessary. Because the telemetric orthopaedic implant described herein has a memory function, patient data may be stored thus allowing for the easy transmission of the data. This data could include personal data, patient history information, as well as patient activity. If the activity is captured, the surgeon could discern if the patient has been accurately performing postoperative rehabilitation regimens. This allows the surgeon to accurately predict and prescribe further regimens, which currently is not feasible with existing employed technology.

Figure 27:
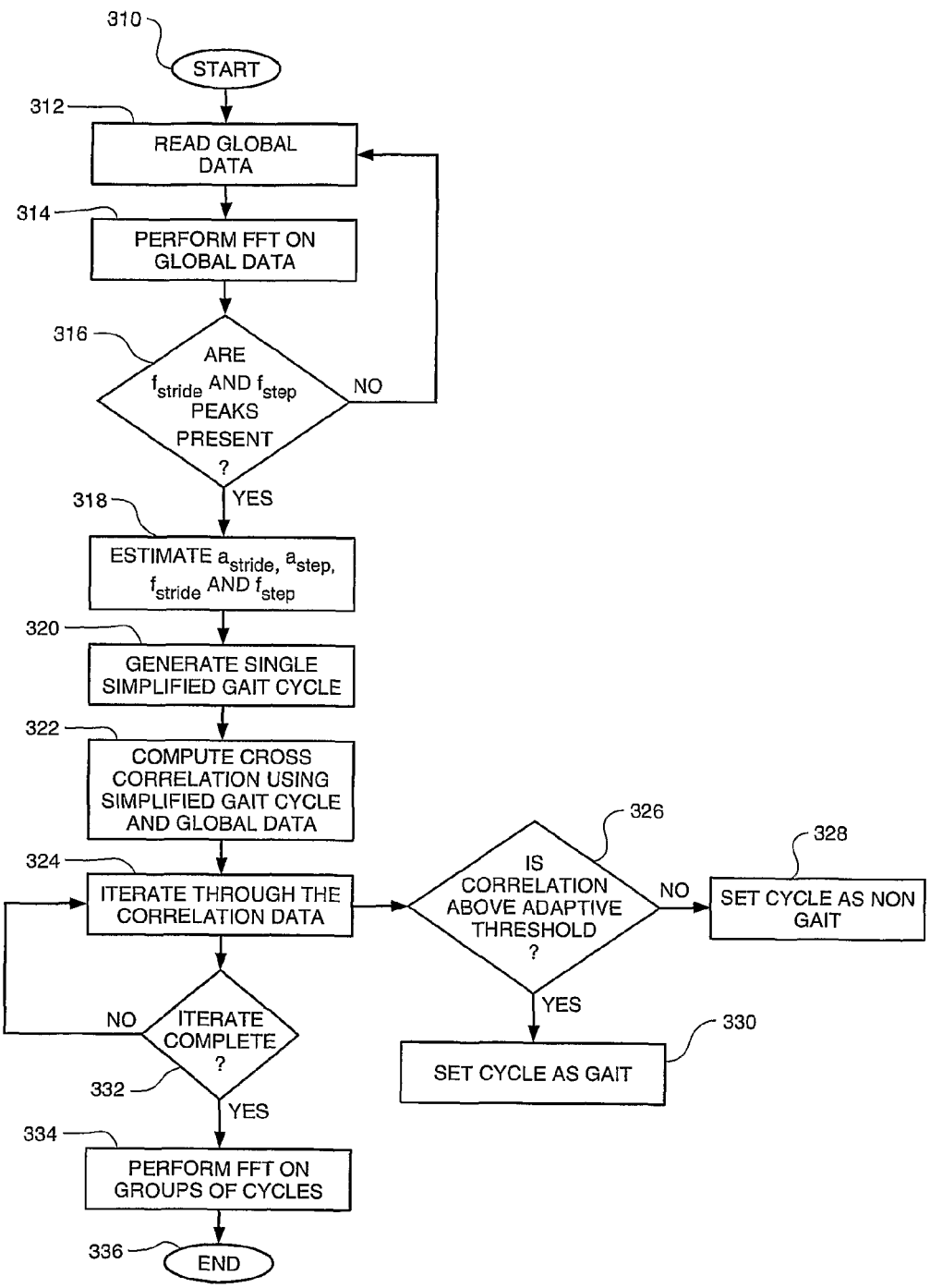
FIG. 27 is a flowchart illustrating steps to analyze gait.

FIG. 27 illustrates steps to implement gait analysis. A person, such as a doctor or healthcare provider, begins at step 310. In step 312, the person reads the data from the patient. For example, the patient may have an active telemetric orthopaedic that continuously measures data as the patient ambulates. In the case of an intramedullary nail as an example, the acceleration of the implant is recorded as the patient ambulates. The surgeon or other healthcare provider may download the data from the implant or control unit in a clinical setting. After the data is downloaded, it is processed in step 314 to convert the data from the time domain to the frequency domain. This allows the doctor, healthcare provider, or software to look for biometric markers or patterns.

Because data is continuously monitored, extraneous data is also downloaded in step 312. For example, data may be recorded when the patient is sitting. In optional step 316, a decision is used to look for peak stride and peak step data within the global download. By utilizing the decision 316, it can be ensured that gait information is present in the global data. If gait information is not present, the doctor or healthcare provider returns to step 312 at another time to retrieve global data.

In step 318 to 332, the gait information is extracted and placed into groups for analysis. In this way, it can be ensured that the doctor or healthcare provider is looking at how the gait changes from one group to the next. For example, the first group of gait information may be from a first time period and the second group of gait information may be from a second time period.

In step 318, stride amplitude, step amplitude, stride frequency, and step frequency is estimated. In step 320, a simplified single gait cycle group is generated. The global data is broken down and correlated to the simplified single gait cycle group in step 322. The data is processed iteratively in step 324. In step 326, a decision is made whether the correlation is above an adaptive threshold. If so, the correlated cycle is identified as a gait group in step 330. If not, the cycle is determined to be non-gait data in step 328. The data is processed iteratively until all the data is analyzed as being gait data or non-gait data in step 332. Once the gait cycles are identified, the gait cycles are analyzed in step 334 and the process completes in step 336.

Alternatively, gait data may be collected and analyzed at the hospital or healthcare facility. In other words, the patient ambulates and data is recorded in the presence of a doctor or healthcare provider. However, this type of data collection does not allow for analysis over long periods of time. Moreover, this type of data collection does not allow for measurement of patient compliance because a patient is more likely to be non-compliant when outside of the hospital or healthcare facility and compliant when in the presence of the doctor or healthcare provider. However, gait data taken at discrete periods of time still provide an indication whether or not a fracture is progressing to a union condition.

CONCLUSION

Although the depicted embodiments concentrate on the function of an instrumented intramedullary nail designed specifically for bone healing, alternative embodiments include incorporation of the sensor and other electronic components within other implantable trauma products, such as a plate, a bone screw, a cannulated screw, a pin, a rod, a staple and a cable. Further, the instrumentation described herein is extendable to joint replacement implants, such a total knee replacements (TKR) and total hip replacements (THR), dental implants, and craniomaxillofacial implants.

A patient receives a wireless instrumented joint reconstruction product. The electromechanical system within the implant may be used to monitor patient recovery using one or more sensors, and make a decision as to whether any intervention is required in the patient's rehabilitation. The telemetric joint replacement continuously measures a complete set of strain values generated in the implant and transmits them from the patient to a laboratory computer system without disturbing the primary function of the implant. Alternatively, a wired system may be utilized in the form of a wearable device external to the patient. Again, the electromechanical system could be designed to monitor various aspects of the patient's recovery.

The wireless technology may be introduced into dental implants to enable early detection of implant overloading. Overloading occurs when prolonged excessive occlusal forces applied to the implant exceeded the ability of the bone-implant interface to withstand and adapt to these forces, leading to fibrous replacement at the implant interface, termed "osseodisintegration," and ultimately to implant failure. Again, a communication link may be used to selectively access the strain data in the memory from an external source.

The technology associated with the instrumentation procedure also may be adapted to monitor soft tissue repair (e.g. skin muscle, tendons, ligaments, cartilage etc.) and the repair and monitoring of internal organs (kidney's, liver, stomach, lungs, heart, etc.).

The advantage of the invention over the prior art concerns the incorporation of the components within the fixation device in a manner that protects the components, provides an accurate and stable connection between the sensor and its environment, maintains the functionality of the implant itself, and is suitable for large scale manufacture. The device allows for information to be gathered and processed yielding useful clinical data with respect to a patient's bone healing cascade.

The instrumented device removes the guessing from the conventional diagnostic techniques, such as x-ray, CT and MRI imaging, by providing the patient objective quantitative data collected from them through the healing process. Currently, there is no device which quantifies the skeletal loads encountered during fracture healing, as well as during different patient and physiotherapy activities. Furthermore, the load distribution between the implant and the adjacent bone during fracture healing is also unknown. Such data would help to optimize postoperative protocols for improved fracture healing. The device described herein addresses this by having on board sensors and a memory facility enabling patient data to be stored thus allowing for early transmission of data. This data includes patient history and patient activity. The device also enables early intervention by the surgeon, if required, such as administration of drugs, injection of orthobiologics, cements or demineralized bone matrix to help promote/accelerate bone healing or a revision surgery.

In view of the foregoing, it will be seen that the several advantages of the invention are achieved and attained. Among other things, potential clinical benefits include reduced number of clinic visits, reduced pain suffered by the patient, improved data on fracture healing, and early notification of delayed or non-union.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A telemetric orthopaedic implant system, the system comprising:
   a. an orthopaedic implant, the orthopaedic implant comprising:
      i. at least one sensor;
      ii. a first recess adapted to receive said at least one sensor;
      iii. an electronic component electrically connected to said at least one sensor, the electronic component including at least a power supply, a first transmitter, a first receiver, and a first microprocessor;
      iv. a second recess adapted to receive the electronic component;
      v. potting material to seal said first recess and said second recess;
      vi. a power source electrically connected to said electronic component; and
      vii. an acting unit electrically connected to said electronic component, said acting unit adapted to carry out a function based upon a condition; and
   b. a control unit, the control unit comprising:
      i. a second microprocessor;
      ii. a second transmitter electrically connected to said second microprocessor, the second transmitter adapted to send a signal to said first receiver of said electronic component; and
      iii. a second receiver electrically connected to said second microprocessor, the second receiver adapted to receive data from said first transmitter of said electronic component.

2. The telemetric orthopaedic implant system of claim 1, wherein said orthopaedic implant is an intramedullary nail.

3. The telemetric orthopaedic implant system of claim 1, wherein said at least one sensor is selected from the group consisting of a foil strain gauge, a semi-conductor strain gauge, a vibrating beam sensor, a force sensor, a piezoelectric element, a fibre Bragg grating, and a giant magneto-impedance (GMI) sensor.

4. The telemetric orthopaedic implant system of claim 1, wherein said control unit further comprises a graphical user interface.

5. The telemetric orthopaedic implant system of claim 1, wherein said orthopaedic implant further comprises a cap insert.

6. The telemetric orthopaedic implant system of claim 1, wherein said first transmitter and said first receiver are combined into a single first transceiver, and second transmitter and second receiver are combined into a single second transceiver.

7. The telemetric orthopaedic implant system of claim 1, further comprising a handheld device.

8. The telemetric orthopaedic implant system of claim 1, further comprising a reader.

9. The telemetric orthopaedic implant system of claim 1, further comprising a computing device.

10. The telemetric orthopaedic implant system of claim 1, further comprising a gait analysis tool.

11. The telemetric orthopaedic implant system of claim 1, wherein said function is delivery of a stored deliverable.

12. The telemetric orthopaedic implant system of claim 1, wherein said condition is based upon data acquired by said at least one sensor.

13. The telemetric orthopaedic implant system of claim 1, wherein said condition is based upon a command provided by said control unit.

14. The telemetric orthopaedic implant system of claim 1, wherein said at least one sensor is selected from the group consisting of a strain gauge, a pH sensor, a temperature sensor, a pressure sensor, a flow sensor, an accelerometer, a gyroscope, an acoustic sensor, a voltage sensor, a pulse meter, an image capturing device, a biomarker indicator, chemical detector, and a biologic indicator.

15. The telemetric orthopaedic implant system of claim 14, wherein said a biomarker indicator is a specific protein indicator.

16. The telemetric orthopaedic implant system of claim 14, wherein said chemical detector is selected from the group consisting of an oxygen detector, an oxygen potential detector, and a carbon dioxide detector.

17. The telemetric orthopaedic implant system of claim 1, wherein said power source is selected from the group consisting of a battery, an energy scavenging device, and an inductive power source.

18. The telemetric orthopaedic implant system of claim 17, wherein said energy scavenging device is selected from the group consisting of a motion powered piezoelectric device and an electromagnetic generator.

19. The telemetric orthopaedic implant system of claim 17, further comprising a charge storage device electrically connected to said energy scavenging device.

20. The telemetric orthopaedic implant system of claim 18, further comprising a charge storage device electrically connected to said energy scavenging device.

* * * * *